United States Patent
Philips et al.

(10) Patent No.: US 7,767,417 B2
(45) Date of Patent: Aug. 3, 2010

(54) PRENYL-ELECTROSTATIC SWITCH, AND METHODS OF USE

(75) Inventors: Mark R. Philips, New York, NY (US); Trever G. Bivona, New York, NY (US)

(73) Assignee: New York University, New York, NY (US)

( * ) Notice: Subject to any disclaimer, the term of this patent is extended or adjusted under 35 U.S.C. 154(b) by 727 days.

(21) Appl. No.: 11/109,262

(22) Filed: Apr. 19, 2005

(65) Prior Publication Data

US 2006/0083742 A1    Apr. 20, 2006

Related U.S. Application Data

(60) Provisional application No. 60/563,651, filed on Apr. 20, 2004, provisional application No. 60/599,533, filed on Aug. 6, 2004.

(51) Int. Cl.
*C12P 21/06* (2006.01)
*A61K 38/48* (2006.01)
*A61K 39/395* (2006.01)
*C07H 21/04* (2006.01)
*C07K 14/32* (2006.01)

(52) U.S. Cl. .............. 435/69.1; 424/138.1; 424/155.1; 435/325; 530/350; 530/388.8; 514/12

(58) Field of Classification Search .............. 424/138.1, 424/155.1; 435/69.1, 325; 514/12; 530/350, 530/388.8
See application file for complete search history.

(56) References Cited

U.S. PATENT DOCUMENTS

| | | | |
|---|---|---|---|
| 3,867,517 | A | 2/1975 | Ling |
| 3,940,475 | A | 2/1976 | Gross |
| 4,237,224 | A | 12/1980 | Cohen et al. |
| 4,289,747 | A | 9/1981 | Chu |
| 4,302,438 | A | 11/1981 | Zech |
| 4,376,110 | A | 3/1983 | David et al. |

OTHER PUBLICATIONS

Elad et al. 1999. Targeting of K-Ras 4B by S-trans,trans-farnesyl thiosalicylic acid. Biochimica et Biophysica Acta, vol. 1452, pp. 228-242.*
Ballester et al., "Phorbol Ester- and Protein Kinase C-Mediated Phosphorylation of the Cellular Kirsten Ras Gene Product," *J. Biol. Chem.* 262:2688-2695 (1987).
Bivona et al., "Phospholipase Cgamma Activates Ras on the Golgi Apparatus by Means of RasGRP1," *Nature* 424:694-698 (2003) (abstract only).
Bos, "Ras Oncogenes in Human Cancer: A Review," *Cancer Res.* 49:4682-4689 (1989).
Chiu et al., "Ras Signalling on the Endoplasmic Reticulum and the Golgi," *Nat. Cell Biol.* 4:343-350 (2002) (abstract only).
Choy et al., "Endomembrane Trafficking of Ras: The CAAX Motif Targets Proteins to the ER and Golgi," *Cell* 98:69-80 (1999) (abstract only).
Cox et al., "The Dark Side of Ras: Regulation of Apoptosis," *Oncogene* 22:8999-9006 (2003).
Greenwood et al., "The Preparation of $^{131}$I-Labelled Human Growth Hormone of High Specific Radioactivity," *Biochem. J.* 89:114-123 (1963).
Hancock et al., "A Polybasic Domain or Palmitoylation is Required in Addition to the CAAX Motif to Localize p21$^{ras}$ to the Plasma Membrane," *Cell* 63:133-139 (1990) (abstract only).
Jackson et al., "Polylysine Domain of K-Ras 4B Protein is Crucial for Malignant Transformation," *Proc. Natl. Acad. Sci. USA* 91:12730-12734 (1994).
Khokhlatchev et al., "Identification of a Novel Ras-Regulated Proapoptotic Pathway," *Curr. Biol.* 12:253-265 (2002) (abstract only).
Kortmansky et al., "Bryostatin-1: A Novel PKC Inhibitor in Clinical Development," *Cancer Invest.* 21:924-936 (2003) (abstract only).
Lang et al., "Protein Kinase A Phosphorylation of RhoA Mediates the Morphological and Functional Effects of Cyclic AMP in Cytotoxic Lymphocytes," *EMBO J.* 15:510-519 (1996).
Lerosey et al., "The cAMP-Dependent Protein Kinase Phosphorylates the Rap1 Protein In Vitro as well as in Intact Fibroblasts, but not the Closely Related Rap2 Protein," *Biochem. Biophys. Res. Commun.* 175:430-436 (1991) (abstract only).
Marchalonis, "An Enzymic Method for the Trace Iodination of Immunoglobulins and other Proteins," *Biochem. J.* 113:299-305 (1969).
McLaughlin et al., "The Myristoyl-Electrostatic Switch: A Modulator of Reversible Protein-Membrane Interactions," *Trends Biochem. Sci.* 20:272-276 (1995).
Quilliam et al., "Rap1 A is a Substrate for Cyclic AMP-Dependent Protein Kinase in Human Neutrophils," *J. Immunol.* 147:1628-1635 (1991) (abstract only).
Sidhu et al., "Ca2+/Calmodulin Binds and Dissociates K-RasB from Membrane," *Biochem. Biophys. Res. Commun.* 304:655-660 (2003) (abstract only).

(Continued)

*Primary Examiner*—Jon P Weber
*Assistant Examiner*—Kailash C Srivastava
(74) *Attorney, Agent, or Firm*—Nixon Peabody LLP

(57) ABSTRACT

The present invention relates to a method of identifying compounds as candidate drugs for treatment of cancer by providing a cell expressing a GTPase protein that is regulated by a prenyl-electrostatic switch, contacting the cell with compounds to be evaluated, and selecting compounds able to regulate charge at the prenyl-electrostatic switch in the GTPase protein as candidate drugs for treatment of cancer. Also disclosed are methods of treating cancer in a patient. An isolated antibody which binds to a phosphorylated prenyl-electrostatic switch on a K-Ras4B protein is also disclosed, as is a kit for detecting phosphorylation of a prenyl-electrostatic switch in a K-Ras4B protein which includes a labeled antibody and a device to detect the label. Also disclosed is a method of detecting phosphorylation of a prenyl-electrostatic switch on a K-Ras4B protein in a biological sample.

17 Claims, 7 Drawing Sheets

OTHER PUBLICATIONS

Szallasi et al., "Differential Regulation of Protein Kinase C Isozymes by Bryostatin 1 and Phorbol 12-Myristate 13-Acetate in NIH 3T3 Fibroblasts," *J. Biol. Chem.* 269:2118-2124 (1994).

Villalonga et al., "Calmodulin Binds to K-Ras, but not to H- or N-Ras, and Modulates Its Downstream Signaling," *Mol. Cell. Biol.* 21:7345-7354 (2001).

Vos et al., "RASSF2 is a Novel K-Ras-Specific Effector and Potential Tumor Suppressor," *J. Biol. Chem.* 278:28045-28051 (2003).

Zhang et al., "Binding of Peptides with Basic and Aromatic Residues to Bilayer Membranes: Phenylalanine in the Myristoylated Alanine-Rich C Kinase Substrate Effector Domain Penetrates Into the Hydrophobic Core of the Bilayer," *J. Biol. Chem.* 278:21459-21466 (2003).

* cited by examiner

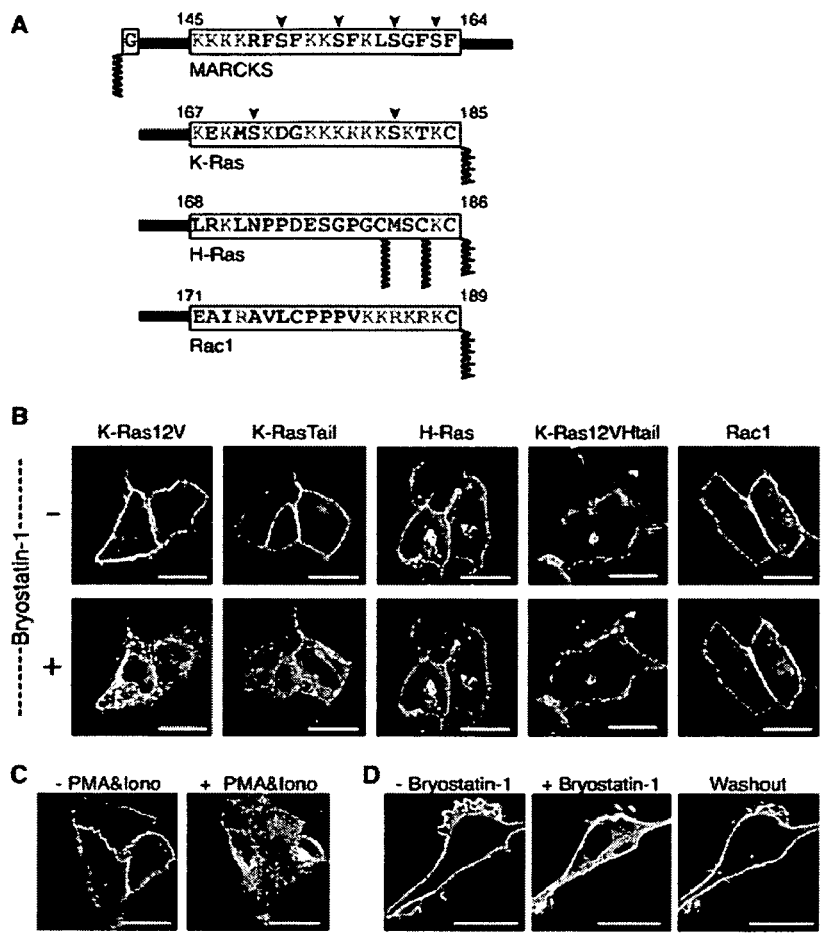
Figures 1A-D

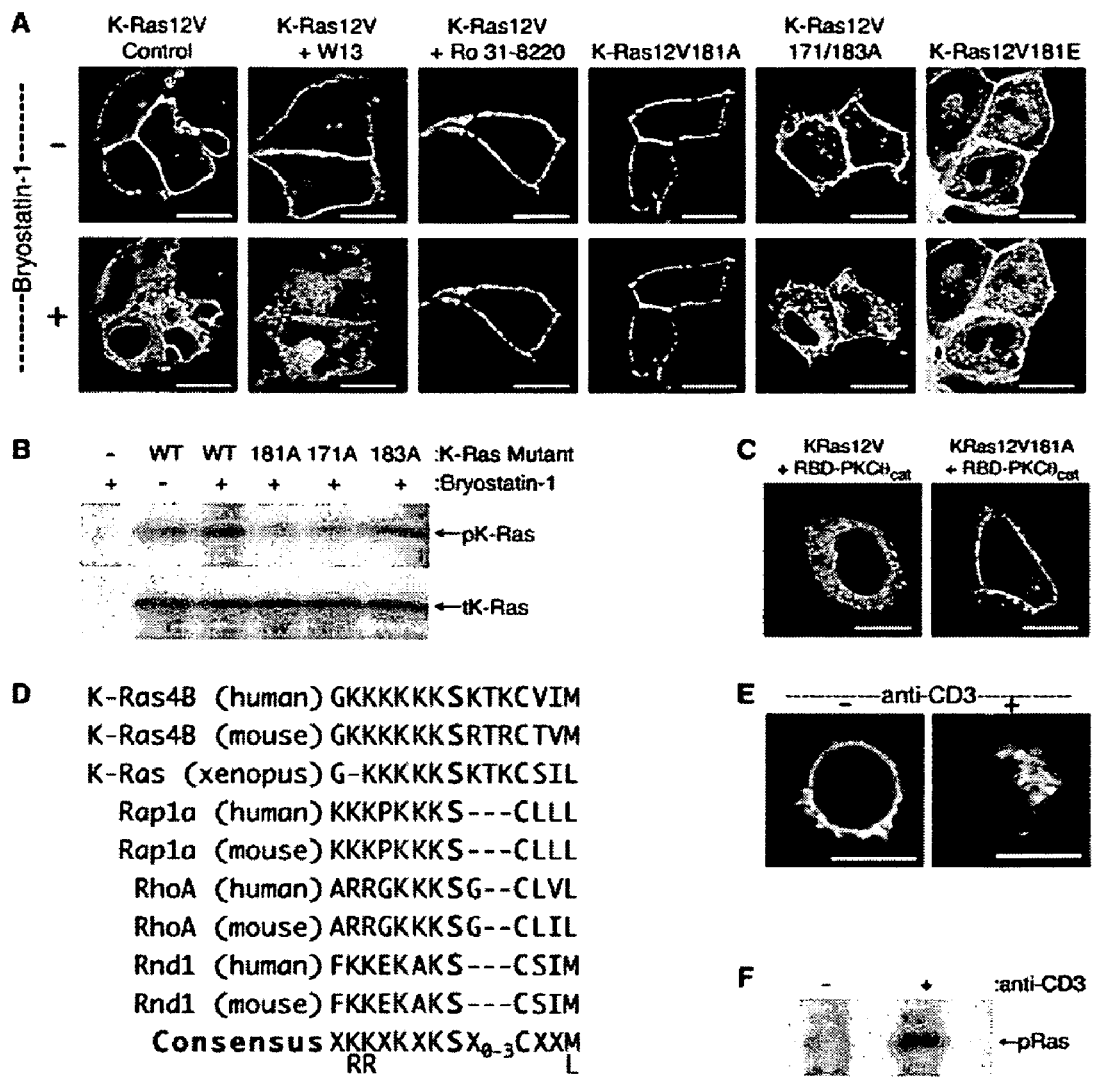
Figures 2A-F

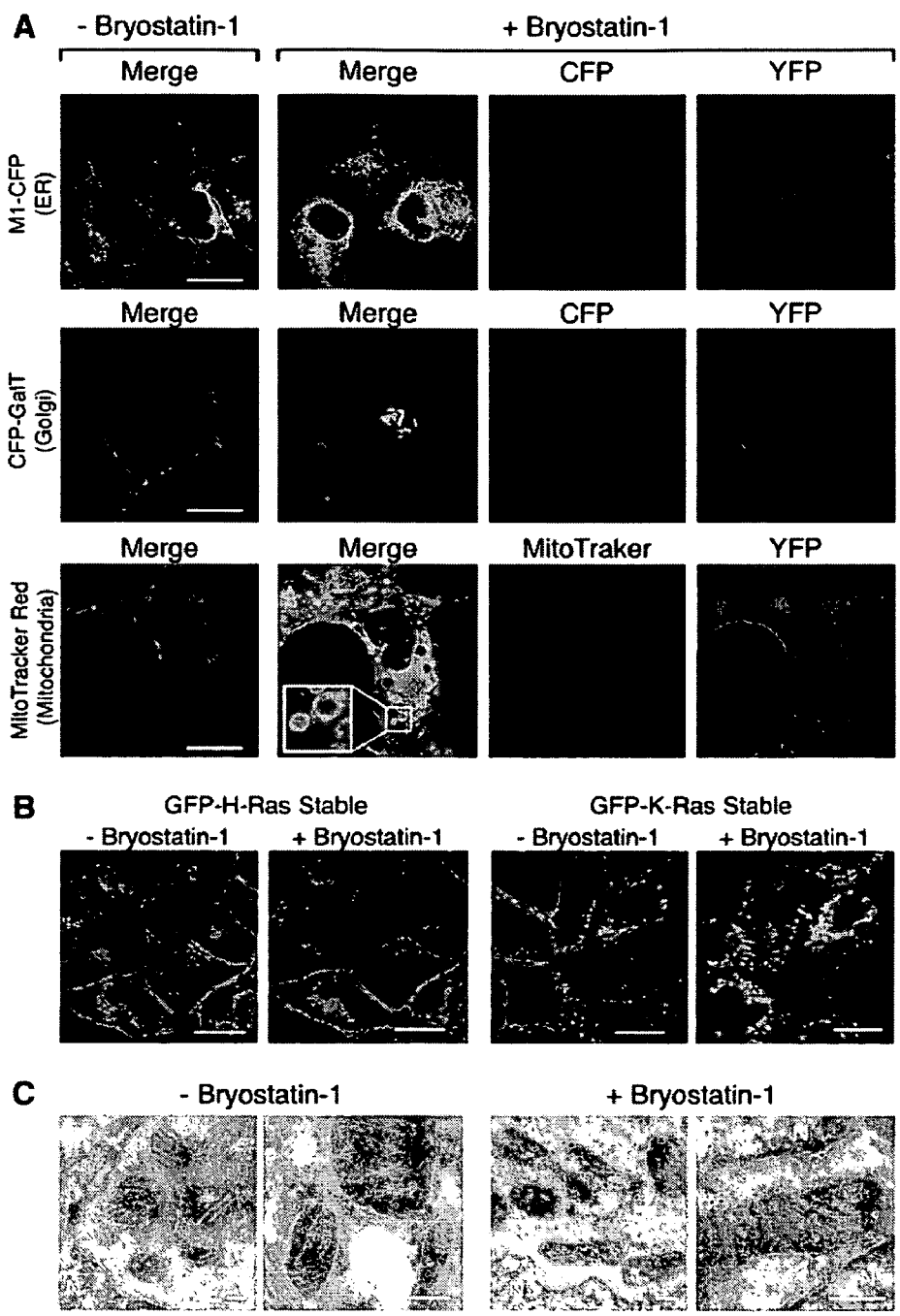
Figures 3A-C

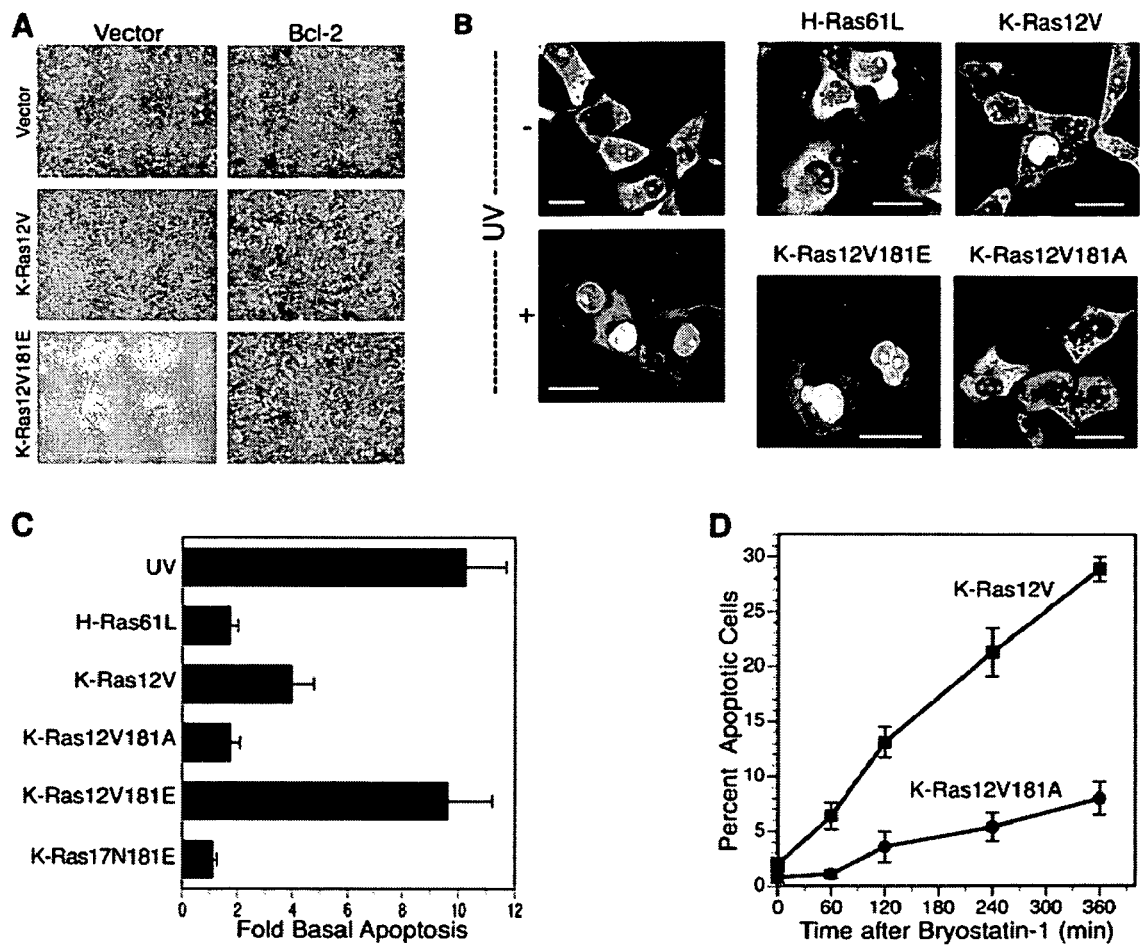
Figures 4A-D

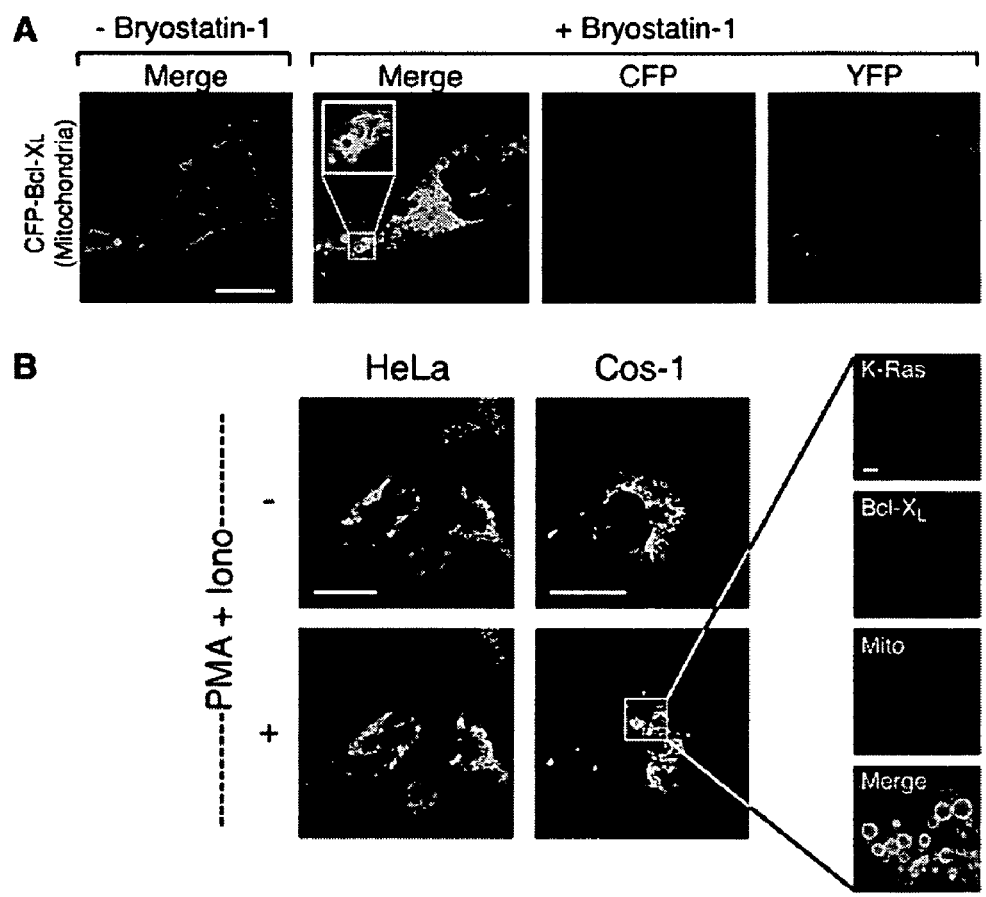
Figures 5A-B

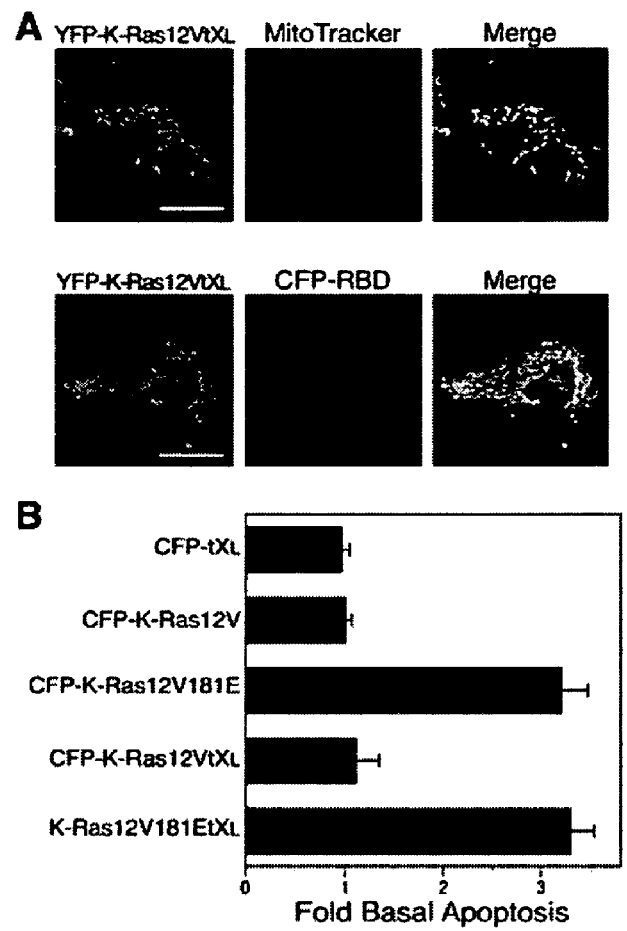
Figures 6A-B

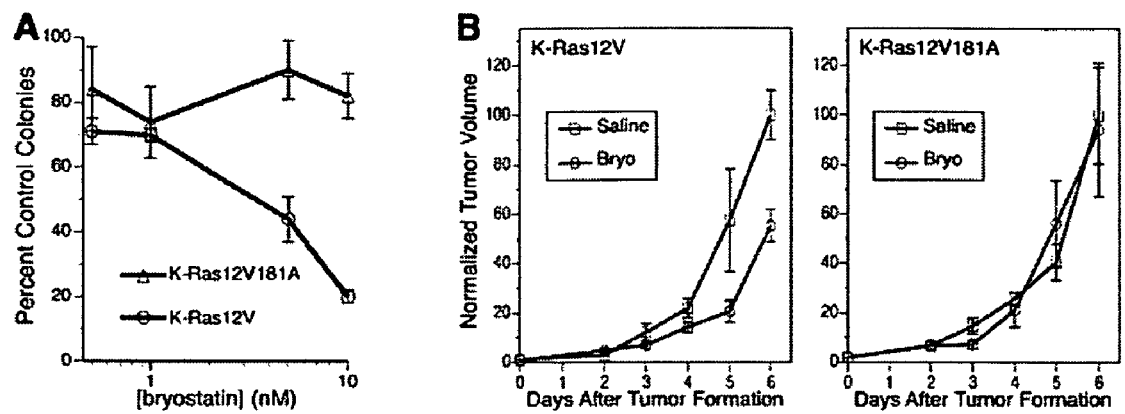
Figures 7A-B

SEQUENCE LISTING

```
<160> NUMBER OF SEQ ID NOS: 14

<210> SEQ ID NO 1
<211> LENGTH: 19
<212> TYPE: PRT
<213> ORGANISM: Human

<400> SEQUENCE: 1

Lys Lys Lys Lys Arg Phe Ser Phe Lys Lys Ser Phe Lys Leu Ser Gly
 1               5                  10                  15

Phe Ser Phe

<210> SEQ ID NO 2
<211> LENGTH: 19
<212> TYPE: PRT
<213> ORGANISM: Human

<400> SEQUENCE: 2

Lys Glu Lys Met Ser Lys Asp Gly Lys Lys Lys Lys Lys Lys Ser Lys
 1               5                  10                  15

Thr Lys Cys

<210> SEQ ID NO 3
<211> LENGTH: 19
<212> TYPE: PRT
<213> ORGANISM: Human

<400> SEQUENCE: 3

Leu Arg Lys Leu Asn Pro Pro Asp Glu Ser Gly Pro Gly Cys Met Ser
 1               5                  10                  15

Cys Lys Cys

<210> SEQ ID NO 4
<211> LENGTH: 19
<212> TYPE: PRT
<213> ORGANISM: Human

<400> SEQUENCE: 4

Glu Ala Ile Arg Ala Val Leu Cys Pro Pro Pro Val Lys Lys Arg Lys
 1               5                  10                  15

Arg Lys Cys

<210> SEQ ID NO 5
```

```
<211> LENGTH: 15
<212> TYPE: PRT
<213> ORGANISM: Human

<400> SEQUENCE: 5

Gly Lys Lys Lys Lys Lys Lys Ser Lys Thr Lys Cys Val Ile Met
 1               5                  10                  15

<210> SEQ ID NO 6
<211> LENGTH: 15
<212> TYPE: PRT
<213> ORGANISM: Mouse

<400> SEQUENCE: 6

Gly Lys Lys Lys Lys Lys Lys Ser Arg Thr Arg Cys Thr Val Met
 1               5                  10                  15

<210> SEQ ID NO 7
<211> LENGTH: 14
<212> TYPE: PRT
<213> ORGANISM: xenopus

<400> SEQUENCE: 7

Gly Lys Lys Lys Lys Lys Ser Lys Thr Lys Cys Ser Ile Leu
 1               5                  10

<210> SEQ ID NO 8
<211> LENGTH: 12
<212> TYPE: PRT
<213> ORGANISM: Human

<400> SEQUENCE: 8

Lys Lys Lys Pro Lys Lys Ser Cys Leu Leu Leu
 1               5                  10

<210> SEQ ID NO 9
<211> LENGTH: 12
<212> TYPE: PRT
<213> ORGANISM: Mouse

<400> SEQUENCE: 9

Lys Lys Lys Pro Lys Lys Ser Cys Leu Leu Leu
 1               5                  10

<210> SEQ ID NO 10
<211> LENGTH: 13
<212> TYPE: PRT
<213> ORGANISM: Human

<400> SEQUENCE: 10

Ala Arg Arg Gly Lys Lys Ser Gly Cys Leu Val Leu
 1               5                  10

<210> SEQ ID NO 11
<211> LENGTH: 13
<212> TYPE: PRT
<213> ORGANISM: Mouse

<400> SEQUENCE: 11

Ala Arg Arg Gly Lys Lys Ser Gly Cys Leu Ile Leu
 1               5                  10

<210> SEQ ID NO 12
<211> LENGTH: 12
<212> TYPE: PRT
```

<213> ORGANISM: Human

<400> SEQUENCE: 12

Phe Lys Lys Glu Lys Ala Lys Ser Cys Ser Ile Met
 1               5                  10

<210> SEQ ID NO 13
<211> LENGTH: 12
<212> TYPE: PRT
<213> ORGANISM: Mouse

<400> SEQUENCE: 13

Phe Lys Lys Glu Lys Ala Lys Ser Cys Ser Ile Met
 1               5                  10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:  consensus
      sequence
<220> FEATURE:
<221> NAME/KEY: VARIANT
<222> LOCATION: (1)
<223> OTHER INFORMATION: Xaa at position 1 is any amino acid
<220> FEATURE:
<221> NAME/KEY: VARIANT
<222> LOCATION: (2)
<223> OTHER INFORMATION: Xaa at position 2 is Lys or Arg
<220> FEATURE:
<221> NAME/KEY: VARIANT
<222> LOCATION: (3)
<223> OTHER INFORMATION: Xaa at position 3 is Lys or Arg
<220> FEATURE:
<221> NAME/KEY: VARIANT
<222> LOCATION: (4)
<223> OTHER INFORMATION: Xaa at position 4 is any amino acid
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (9)
<223> OTHER INFORMATION: Xaa at position 9 is any amino acid or is
      missing
<220> FEATURE:
<221> NAME/KEY: VARIANT
<222> LOCATION: (10)
<223> OTHER INFORMATION: Xaa at position 10 is any amino acid or is
      missing
<220> FEATURE:
<221> NAME/KEY: VARIANT
<222> LOCATION: (11)
<223> OTHER INFORMATION: Xaa at position 11 is any amino acid or is
      missing
<220> FEATURE:
<221> NAME/KEY: VARIANT
<222> LOCATION: (13)
<223> OTHER INFORMATION: Xaa at position 13 is any amino acid
<220> FEATURE:
<221> NAME/KEY: VARIANT
<222> LOCATION: (14)
<223> OTHER INFORMATION: Xaa at position 14 is any amino acid
<220> FEATURE:
<221> NAME/KEY: VARIANT
<222> LOCATION: (15)
<223> OTHER INFORMATION: Xaa at position 15 is Met or Leu

<400> SEQUENCE: 14

Xaa Xaa Xaa Xaa Lys Xaa Lys Ser Xaa Xaa Xaa Cys Xaa Xaa Xaa
 1               5                  10                  15

PRENYL-ELECTROSTATIC SWITCH, AND METHODS OF USE

This application claims the priority benefit of U.S. Provisional Patent Application Ser. No. 60/563,651, filed Apr. 20, 2004, and U.S. Provisional Patent Application Ser. No. 60/599,533, filed Aug. 6, 2004, each of which is hereby incorporated by reference in its entirety.

The subject matter of this application was made with support from the United States Government under National Institutes of Health Grant No. RO1 GM55279. The United States Government may have certain rights.

FIELD OF THE INVENTION

This invention relates to a prenyl-electrostatic switch in GTPase proteins, a method of identifying compounds as candidate drugs for treatment of cancer, methods of treating cancer in a patient, an isolated antibody which binds a GTPase protein, and a method of detecting phosphorylation of a prenyl-electrostatic switch on a GTPase protein.

BACKGROUND OF THE INVENTION

GTP-binding proteins ("GTPases") are a family of regulatory proteins that act as molecular switches. GTPases control a wide range of biological processes including: receptor signaling, intracellular signal transduction pathways, and protein synthesis. Their activity is regulated by factors that control their ability to bind GTP and hydrolyze it to GDP.

A group of GTPase proteins, named for their association with rat sarcomas (ras), was originally isolated from Harvey (H-ras, Ha-ras, rasH) and Kirsten (K-ras, Ki-ras, rasK) murine sarcoma viruses. Ras genes are widely conserved among animal species, and sequences corresponding to both H-ras and K-ras genes have been detected in human, avian, murine, and non-vertebrate genomes. The closely related N-ras gene was originally detected in human neuroblastoma and sarcoma cell lines. All genes of the family have a similar exon-intron structure and each encodes a p21 protein.

Although mammalian genomes contain three ras genes, mutations in kras are most frequently associated with human cancer (Bos, "Ras Oncogenes in Human Cancer: A Review," *Cancer Res.* 49:4682-4689 (1989)). Therefore, properties that are specific to K-Ras are of particular significance to cancer biologists since they might be exploited in the development of anti-cancer drugs. The differential biology of Ras isoforms is generated, in large part, by distinct membrane targeting sequences. Membrane association of all Ras isoforms requires prenylation (i.e., farnesylation), proteolysis, and carboxyl methylation of a C-terminal CAAX motif. Plasma membrane targeting of the principal splice variant of K-Ras also requires a unique polybasic region adjacent to the CAAX motif (Hancock et al., "A Polybasic Domain or Palmitoylation is Required in Addition to the CAAX Motif to Localize p21$^{ras}$ to the Plasma Membrane," *Cell* 63:133-139 (1990); Jackson et al., "Polylysine Domain of K-Ras 4B Protein is Crucial for Malignant Transformation," *Proc. Natl. Acad. Sci. USA* 91:12730-12734 (1994); Choy et al., "Endomembrane Trafficking of Ras: The CAAX Motif Targets Proteins to the ER and Golgi," *Cell* 98:69-80 (1999)).

K-Ras thus falls into a broad class of proteins that are anchored to the cytoplasmic face of the plasma membrane by virtue of post-translational modification with lipids that act in conjunction with polybasic stretches of polypeptide. Whereas the lipid moieties are thought to insert into the phospholipid bilayer, the polybasic regions are believed to associate with the anionic head groups of inner leaflet phospholipids (Leventis et al., "Lipid-Binding Characteristics of the Polybasic Carboxy-Terminal Sequence of K-Ras4B," *Biochemistry* 37:7640-7648 (1998)). Included in this class of proteins is the myristoylated alanine-rich C kinase substrate ("MARCKS") that associates with the plasma membrane via an N-terminal myristoyl modification and a polybasic region. Serine residues within the polybasic region are sites for PKC-mediated phosphorylation (FIG. 1A) that neutralize the charge and thereby cause the MARCKS protein to dissociate from the plasma membrane. The mechanism by which MARCKS is discharged from the plasma membrane through phosphorylation has been referred to as a myristoyl-electrostatic switch (McLaughlin et al., "The Myristoyl-Electrostatic Switch: A Modulator of Reversible Protein-Membrane Interactions," *Trends Biochem. Sci.* 20:272-276 (1995)).

Like MARCKS, the polybasic region of K-Ras harbors three potential phosphorylation sites and this segment has previously been shown to be phosphorylated by PKC (Ballester et al., "Phorbol Ester- and Protein Kinase C-Mediated Phosphorylation of the Cellular Kirsten Ras Gene Product," *J. Biol. Chem.* 262:2688-2695 (1987)). K-Ras was therefore tested for an electrostatic switch analogous to that of MARCKS (McLaughlin et al., "The Myristoyl-Electrostatic Switch: A Modulator of Reversible Protein-Membrane Interactions," *Trends Biochem. Sci.* 20:272-276 (1995)).

The present invention is directed to determining whether K-Ras has a prenyl-electrostatic switch and, if so, the use of such a switch.

SUMMARY OF THE INVENTION

One aspect of the present invention relates to a method of identifying compounds as candidate drugs for treatment of cancer. This method involves providing a cell expressing a GTPase protein that is regulated by a prenyl-electrostatic switch. The cell is contacted with compounds to be evaluated. Compounds able to regulate charge at the prenyl-electrostatic switch in the GTPase protein are selected as candidate drugs for treatment of cancer.

Another aspect of the present invention relates to a method of treating cancer in a patient. This method involves administering a compound able to regulate charge at a prenyl-electrostatic switch in a GTPase protein to a patient under conditions effective to treat cancer.

A further aspect of the present invention relates to a method of treating cancer in a patient. This method involves administering a protein kinase C agonist other than bryostatin-1 to a patient under conditions effective to treat cancer.

Yet another aspect of the present invention relates to an isolated antibody which binds to a phosphorylated prenyl-electrostatic switch in a GTPase protein.

Still another aspect of the present invention relates to a kit for detecting phosphorylation of a prenyl-electrostatic switch in a K-Ras4B protein. The kit includes an isolated antibody which binds to a phosphorylated prenyl-electrostatic switch in a K-Ras4B protein where the antibody is bound to a label, and a device to detect the label.

A further aspect of the present invention relates to a method of detecting phosphorylation of a prenyl-electrostatic switch on a GTPase protein in a biological sample. This method involves providing an antibody which binds to a phosphorylated prenyl-electrostatic switch on a K-Ras4B protein. The antibody is contacted with the biological sample. Binding that occurs between the biological sample and the antibody is detected to identify phosphorylation of a prenyl-electrostatic switch on the GTPase protein.

The present invention demonstrates that serines 171 and 181 within the C-terminal polybasic region of K-Ras are substrates for protein kinase C ("PKC") and that phosphorylation of serine 181 regulates association with the plasma membrane. The C-terminus of K-Ras thus constitutes a prenyl-electrostatic switch. It is further shown that phosphorylated K-Ras dissociated from the plasma membrane becomes rapidly associated with endomembranes, including the cytosolic surface of mitochondria. Internalized K-Ras colocalizes with Bcl-2 and Bcl-XL on mitochondria and induces apoptosis; PKC agonists downregulate K-Ras signaling and inhibit K-Ras-dependent cellular transformation; and growth of K-Ras-dependent tumors in nude mice is inhibited by the PKC agonist bryostatin-1 in a serine 181-dependent fashion. These observations suggest a novel approach to treating K-Ras-dependent tumors with selective PKC agonists.

BRIEF DESCRIPTION OF THE DRAWINGS

FIGS. 1A-D show that PKC agonists stimulate translocation of K-Ras from the plasma membrane to internal membranes. Comparison of the membrane targeting sequences present in the MARCKS protein (SEQ ID NO: 1) with K-Ras (SEQ ID NO: 2), H-Ras (SEQ ID NO: 3) and Rac1 (SEQ ID NO: 4). Arrowheads indicate putative PKC sites. The images of FIG. 1B depict the treatment of MDCK cells with bryostatin-1, which induced rapid translocation (0 and 3 mm images shown) from plasma membrane to endomembranes of GFP-K-Ras12V and GFP extended with the 20 aa C-terminus (tail) of K-Ras, but not of GFP-H-Ras, GFP-K-Ras12V with an H-Ras tail or GFP-Rac1. FIG. 1C is a set of images showing that PMA and ionomycin promote internalization of GFP-K-Ras12V. The images in FIG. 1D show that bryostatin-1-induced internalization (3 min) of GFP-K-Ras12V in COS-1 cells is reversible (10 min washout). The images are representative of >90% of transfected cells (n=10). Bars represent 10 µm.

FIGS. 2A-F show the PKC phosphorylation of K-Ras on Serine 181 to promote internalization. The images of FIG. 2A show the treatment of MDCK cells with bryostatin-1, which induced rapid translocation (0 and 3 mm images shown) from plasma membrane to endomembranes of GFP-K-Ras12V and GFP-K-Ras12V171A183A, but not of GFP-K-Ras12V181A. Pretreatment with the PKC inhibitor Ro-31-8220 blocked, whereas the calmodulin inhibitor W-13 had no effect on translocation. Expression of K-Ras12V181E resulted in constitutive internalization. As illustrated in FIG. 2B, metabolic labeling with [$^{32}$P]orthophosphate demonstrates that bryostatin-1 induced phosphorylation of K-Ras is primarily on serine 181. The set of images shown in FIG. 2C show that expression of RBD-PKC$_{cat}$ promotes constitutive internalization of GFP-K-Ras but not GFP-K-RasS181A. FIG. 2D is a sequence alignment of Ras related GTPases, which reveals potential PKC phosorylation sites (S—phosphorylation site; C—prenylation site). C-terminal sequences of K-Ras4B (human) (SEQ ID NO: 5), K-Ras 4B (mouse) (SEQ ID NO: 6), K-Ras (xenopus) (SEQ ID NO: 7), Rap1a (human) (SEQ ID NO: 8), Rap1a (mouse) (SEQ ID NO: 9), RhoA (human) (SEQ ID NO: 10), RhoA (mouse) (SEQ ID NO: 11), Rnd1 (human) (SEQ ID NO: 12), and Rnd1 (mouse) (SEQ ID NO: 13), are shown, as well as a consensus sequence (SEQ ID NO: 14). The set of images in FIG. 2E show that crosslinking of the antigen receptor stimulated internalization of GFP-K-Ras in Jurkat T cells. FIG. 2F shows that TCR crosslinking stimulated [$^{32}$P] incorporation into endogenous Ras in Jurkat T cells equilibrated with [$^{32}$P]orthophosphate. The images are representative of >90% of transfected cells (n=10) except in FIG. 2E where the image represents 50% of treated cells. Bars represent 10 µm.

FIGS. 3A-C show that phosphorylation promotes its translocation from plasma membrane to endoplasmic reticulum, Golgi, and mitochondria. FIG. 3A shows COS-1 cells expressing YFP-K-Ras12V and the indicated CFP-tagged compartment marker or MitoTracker Red which were imaged before and 6 min after treatment with bryostatin-1. Localization on the outer mitochondrial membrane is shown in the magnified insets around the periphery of MitoTracker Red marked organelles. In the images of FIG. 3B, MDCK cells stably expressing either GFP-H-Ras or GFP-K-Ras at endogenous levels treated with bryostatin-1 reveal that only K-Ras associates with internal membranes including mitochondria marked by MitoTracker Red (Arrow). In FIGS. 3A-B, bars indicate 10 µm. The images of FIG. 3C are anti-Ras immunogold electron micrographs of Jurkat T cells before and after treatment with bryostatin-1. Cytoplasm rich in mitochondria are shown at two magnifications for each condition. The arrow indicates one 10 nm gold particle, N indicates nucleus, and bars represent 200 nm.

FIGS. 4A-D show that K-Ras with a negative charge at position 181 induces apoptosis. In FIG. 4A, expression of K-Ras12V181E in NIH3T3 cells induced cell death that was rescued by co-expression of Bcl-2. The images in FIG. 4B show apoptosis of COS-1 cells (scored with a YFP-tagged caspase 3 sensor) induced by UV irradiation or expression of the indicated Ras constructs. The YFP sensor accumulates in the nucleus as a result of caspase activation. Bars indicate 10 µm. FIG. 4C is a bar graph showing quantification of results shown in FIG. 4B. Nucleotide-free K-Ras17N181E did not promote apoptosis. FIG. 4D is a graph showing that bryostatin-1 stimulated apoptosis in NIH3T3 cells transformed with K-Ras12V but not K-Ras12V181A.

FIGS. 5A-B show that K-Ras on mitochondria associates with Bcl-XL. The images in FIG. 5A illustrate a Cos-1 cell expressing YFP-K-Ras12V and CFP-Bcl-XL before and after (5 min) treatment with bryostatin-1. CFP-Bcl-XL marks the mitochondria and colocalization with YFP-K-Ras12V on this compartment is seen after bryostatin-1. The FRET efficiency between YFP-K-Ras12V and CFP-Bcl-XL on treated mitochondria (inset) was measured as 17±8%. In the images of FIG. 5B, HeLa (left) or COS-1 (right) expressing YFP-K-Ras12V, CFP-Bcl-XL and treated with Mitotracker Red were stimulated with PMA plus ionomycin. The colocalization of CFP-Bcl-XL and treated with Mitotracker Red gave a yellow pseudocolor on the mitochondrial of untreated cells that was converted to the white pseudocolor of triple overlap in treated cells. The inset demonstrates that PKC activation induced colocalization of K-Ras12V with Bcl-XL on the outer membrane of organelles marked by Mitotracker Red. Bars indicate 10 µm.

FIGS. 6A-B show that mitochondrial-targeted K-Ras with a phosphomimetic group at position 181 promotes apoptosis. The images of FIG. 6A show that the 30 aa tail of Bcl-XL targets YFP-tagged K-Ras12V (YFP-K-Ras12VtXL exclusively to mitochondria (upper panels) where its effector domain is free to interact with the Ras binding domain of Raf-1 (CFP-RBD, lower panels). Bars indicate 10 µm. The graph in FIG. 6B illustrates that K-Ras12V targeted to mitochondria with the tail of Bcl-XL requires a negative charge at position 181 to stimulate apoptosis.

FIGS. 7A-B are graphs showing that phosphorylation inhibits K-Ras12V mediated transformation in vitro and in vivo. Serine 181 was required for inhibition by bryostatin-1 of K-Ras12V-dependent growth in soft agar (FIG. 7A), and K-Ras12V-dependent tumor growth in nude mice (FIG. 7B).

In FIG. 7B, tumor volumes are normalized to the average volume on day 6 of tumors in saline-treated animals. Only the curves representing K-Ras12V-dependent tumors±bryostatin-1 (left panel) were statistically different ($p<0.05$, ANOVA).

DETAILED DESCRIPTION OF THE INVENTION

One aspect of the present invention relates to a method of identifying compounds as candidate drugs for treatment of cancer. This method involves providing a cell expressing a GTPase protein that is regulated by a prenyl-electrostatic switch. The cell is contacted with compounds to be evaluated. Compounds able to regulate charge at the prenyl-electrostatic switch in the GTPase protein are selected as candidate drugs for treatment of cancer.

GTP-binding proteins (also called GTPases because of the GTP hydrolysis that they catalyze) constitute a large family of proteins that all have a similar GTP-binding globular domain. When its bound GTP is hydrolyzed to GDP, this domain undergoes a conformational change that inactivates the protein. GTPase proteins suitable for carrying out the methods of the present invention include, without limitation, K-Ras, Rap1a, RhoA, Rnd1, Rnd2, and Rnd3.

In one embodiment, the GTPase protein is K-Ras, such as the K-Ras splice variant K-Ras4B. K-Ras falls into a broad class of proteins that are anchored to the cytoplasmic face of the plasma membrane by virtue of post-translational modification with lipids that act in conjunction with polybasic stretches of polypeptide. Whereas the lipid moieties are thought to insert into the phospholipid bilayer, the polybasic regions are believed to associate with the anionic head groups of inner leaflet phospholipids. Membrane association of all Ras isoforms requires prenylation (i.e., farnesylation), proteolysis, and carboxyl methylation of a C-terminal CAAX motif. Plasma membrane targeting of K-Ras also requires a unique polybasic region of about 20 amino acids adjacent to the CAAX motif.

As demonstrated in the examples, the C-terminal portion of K-Ras has a prenyl-electrostatic switch (also known as a farnesyl-electrostatic switch) which in this case is a serine residue in position 181 of the above-described polybasic region. The serine residue in position 181 is a substrate for protein kinase C, and phosphorylation of serine 181 regulates association of K-Ras with the plasma membrane. Alternatively, the prenyl-electrostatic switch is at least two amino acid residues in the above-described C-terminal portion of the K-Ras protein. In one embodiment, serine residues in positions 171 and 181, respectively, are a substrate for PKC, and phosphorylation of these serine residues regulates K-Ras association with the plasma membrane. In another embodiment, one of the at least two amino acid residues in the C-terminal portion of the K-Ras protein is a threonine residue in position 183 of the K-Ras protein.

In another embodiment, the GTPase protein is a Rap1a protein. Rap1a is a ubiquitously expressed GTPase in the Ras family that regulates a wide variety of cellular processes, including lymphocyte adhesion, and through activation of B-Raf, is involved in cellular transformation.

In a further embodiment, the GTPase protein is a RhoA protein. RhoA is a Ras-related GTPase in the Rho family that regulates the actin cytoskeleton to produce stress fibers and in some contexts is required for Ras-mediated cellular transformation.

In yet another embodiment, the GTPase protein is Rnd1, Rnd2, or Rnd3 protein. Rnd1 is a Rho family GTP binding protein that stimulates disassembly of actin filaments and plays a role in neuronal differentiation. Rnd2 and Rnd3 (also known as RhoE) have similar sequences and are also candidates for GTPases that are regulated by a prenyl-electrostatic switch.

In carrying out the method of identifying compounds of the present invention, a cell is provided which expresses a GTPase protein that is regulated by a prenyl-electrostatic switch. To this end, a nucleic acid molecule encoding a GTPase polypeptide or protein can be introduced into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense ($5' \rightarrow 3'$) orientation and correct reading frame. The vector contains the necessary elements for the transcription and translation of the inserted GTPase protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the GTPase protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes MRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokarvotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expressing vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The GTPase protein-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a GTPase protein is inserted into a vector in the sense (i.e., 5'→3') direction, such that the open reading frame is properly oriented for the expression of the encoded GTPase protein under the control of a promoter of choice. Single or multiple nucleic acids may be ligated into an appropriate vector in this way, under the control of a suitable promoter, to prepare a nucleic acid construct.

Once the isolated nucleic acid molecule encoding the GTPase protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

In all aspects of the present invention "contacting a cell" can be carried out as desired, including, but not limited to, contacting cells in culture with compounds to be selected in a suitable growth medium. Alternatively, mice, rats or other mammals are injected with compounds to be selected.

The step of selecting compounds able to regulate charge at the prenyl-electrostatic switch in the GTPase protein as candidate drugs for treatment of cancer involves selecting compounds capable of neutralizing the net positive charge in the GTPase protein at particular residues herein identified as a prenyl-electrostatic switch. Among the methods of neutralizing the charge is to introduce a phosphate group into the otherwise polybasic region of the protein. Thus, one class of compounds selected would be those that promote phosphorylation of the protein in the region of the prenyl-electrostatic switch. Phosphorylation of the GTPase protein at the prenyl-electrostatic switch results in the release of the GTPase protein from the cell's plasma membrane. Thus, a compound's ability to regulate charge at the prenyl-electrostatic switch of a GTPase protein is determined by detecting dissociation of the GTPase protein from plasma membrane, or alternatively, translocation of the GTPase protein from plasma membrane to intracellular membrane, including, without limitation, nuclear envelope, Golgi apparatus, or mitochondria.

Detection of GTPase translocation may be facilitated by tagging the GTPase protein prior to contacting the cell with a marker protein, and detecting differences in marker protein patterns in the cell before and after carrying out the step of contacting the cell with compounds. By way of example, the method of identifying compounds as candidate drugs for treatment of cancer according to the present invention, may be carried out by providing a cell expressing a GTPase protein that is regulated by a prenyl-electrostatic switch, the GTPase protein being tagged, e.g., by a green fluorescent protein. The cell is then contacted with a library of compounds to be evaluated. The selecting step is carried out using an automated fluorescence microscope to score for a charge in the fluorescence pattern from one of peripheral staining (e.g., chicken wire) to one of diffuse or internal staining. In a variation of this approach, one could counter stain a selected internal compartment and test for delivery of dislodged K-Ras to that compartment by scoring for colocalization. For example, the mitochrondria of the cell expressing the GTPase protein is stained with MitoTraker Red and the automated fluorescence microscope is used to score for a pattern of overlap between green and red probes (GTPase protein and mitochondria).

In one embodiment of the method of identifying compounds of the present invention, the compound is a PKC agonist (i.e., a compound capable of inducing, enhancing, or improving PKC activity). Known PKC agonists include, but are not limited to, diacylglycerol (DAG) analogs such as 1,2-dioctanoyl-sn-glycerol (DOG) and 1-oleoyl-2-acetyl-sn-glycerol (OAG), phorbol esters such as Phorbol-12-myristate-13-acetate (PMA), and naturally occurring metabolites such as gnidimacrin, thymeleatoxin, and bryostatin.

Another aspect of the present invention relates to a method of treating cancer in a patient. This method involves administering a compound able to regulate charge at a prenyl-electrostatic switch in a GTPase protein to a patient under conditions effective to treat cancer.

A further aspect of the present invention relates to a method of treating cancer in a patient. This method involves administering a protein kinase C agonist other than bryostatin-1 to a patient under conditions effective to treat cancer.

Thus, compounds suitable for carrying out the methods of treating cancer in a patient include compounds able to regulate charge at a prenyl-electrostatic switch in a GTPase protein, which may be selected from the method of identifying compounds described supra, or PKC agonists other than bryostatin, as described supra.

"Treating cancer" as used herein, specifically refers to administering therapeutic agents to a patient diagnosed of cancer, i.e., having established cancer in the patient, to inhibit the further growth or spread of the malignant cells in the cancerous tissue, and/or to cause the death of the malignant cells. In particular, breast cancers, colon cancers, prostate cancers, lung cancers and skin cancers may be amenable to the treatment by the methods of the present invention. "Treating cancer" also encompasses treating a patient having premalignant conditions to stop the progression of, or cause regression of, the premalignant conditions. Examples of premalignant conditions include hyperplasia, dysplasia, and metaplasia.

In practicing the methods of treating cancer in a patient of the present invention, the administering step is carried out by administering an agent (i.e., a PKC agonist or a compound able to regulate charge at a prenyl-electrostatic switch in a GTPase protein) orally, intradermally, intramuscularly, intraperitoneally, intravenously, subcutaneously, or intranasally. The agent of the present invention may be administered alone or with suitable pharmaceutical carriers, and can be in solid or liquid form, such as tablets, capsules, powders, solutions, suspensions, or emulsions.

The agent may be orally administered, for example, with an inert diluent, or with an assimilable edible carrier, or it may be enclosed in hard or soft shell capsules, or it may be compressed into tablets, or it may be incorporated directly with food. For oral therapeutic administration, the agent of the present invention may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agent of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

A compound able to regulate charge at a prenyl-electrostatic switch in a GTPase protein, or a PKC agonist, may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Suitable patients for this aspect of the present invention include, without limitation, any mammal, preferably a human.

Another aspect of the present invention relates to an isolated antibody which binds to a phosphorylated prenyl-electrostatic switch in a GTPase protein.

In a preferred embodiment, the isolated antibody of the present invention binds to a phosphorylated prenyl-electrostatic switch on a K-Ras4B protein. A phosphorylated prenyl-electrostatic switch on a K-Ras4B protein to which an isolated antibody of the present invention binds is described supra. The antibody of the present invention preferably reacts specifically with a phospho-serine at a particular site on human K-Ras4B protein, or reacts specifically with a phospho-threonine at a particular site on human K-Ras4B protein, or a combination thereof. The length of suitable immunogenic peptides may vary, but generally the immunogens are about 10-30 amino acids in length, more preferably about 15-20 amino acids in length. Binding regions on K-Ras4B for the antibodies of the present invention may also vary, but at least include residues of the prenyl-electrostatic switch described supra. Preferably, binding residues flank the prenyl-electrostatic switch on the N- and C-terminal sides of K-Ras4B.

In practice, antibodies that bind to phospho-S181-K-Ras4B will have little flexibility in choice of binding regions since serine 181 lies just 4 residues upstream of the C-terminal prenylcysteine. Thus, for example, a 20 amino acid immunogenic peptide would likely consist of residues 166-185 of K-Ras4B that incorporates a phosphoserine at the position corresponding to residue 181 in the full length protein. More flexibility in designing antibodies for phospho-S171-K-Ras4B is available. With respect to the posttranslationally modified C-terminal cysteine of K-Ras4B (the naturally occurring K-Ras4B protein ends in a farnesylcysteine), the antibody will preferably have a farnesylcysteine end. Alternatively, a hydrophobic amino acid, such as isoleucine, may be utilized in place of the farnesylcysteine. Yet another alternative is to ignore the posttranslation processing of the CAAX motif altogether and include the unmodified CVIM sequence (FIG. 8) as the C-terminus of the immunogenic peptide or antibody.

Antibodies of the present invention are capable of binding to at least a portion of a human GTPase protein or polypeptide and may function to inhibit activity of such a protein or polypeptide, or modulate regulation of charge at a prenyl-electrostatic switch on such a protein or polypeptide. Such antibodies may have therapeutic potential, particularly in the treatment of cancer by regulation of charge at a prenyl-electrostatic switch on GTPase protein.

Antibodies of the present invention may be either monoclonal antibodies or polyclonal antibodies. Monoclonal antibody production may be carried out by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., *Nature* 256:495 (1975), which is hereby incorporated by reference in its entirety.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Milstein et al., *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference in its entirety.

In addition to utilizing whole antibodies, the present invention may employ the use of binding portions of such antibodies. Such binding portions include Fab fragments, $F(ab')_2$ fragments, and Fv fragments. These antibody fragments can be made by conventional procedures, such as proteolytic fragmentation procedures, as described in Goding, *Monoclonal Antibodies: Principles and Practice*, pp. 98-118 (N.Y. Academic Press, 1983), which is hereby incorporated by reference in its entirety.

Isolated antibodies of the present invention may be bound to a label. Suitable labels include, without limitation, fluorescent labels, biologically-active labels, radioactive labels, nuclear magnetic resonance active labels, luminescent labels, and chromophore labels. An antibody bound to a label is useful for diagnostic use, such as for detecting the presence or absence of a phosphorylated GTPase protein at its prenyl-electrostatic switch, as described in more detail infra.

Examples of labels useful for diagnostic imaging in accordance with the present invention are radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, Wensel et al., *Radioimmunoimaging and Radioimmunotherapy*, Elsevier, N.Y. (1983), which is hereby incorporated by reference, teach techniques relating to the radiolabeling of antibodies, as does Colcher et al., "Use of Monoclonal Antibodies as Radiopharmaceuticals for the Localization of Human Carcinoma Xenografts in Athymic Mice," *Meth. Enzymol.* 121: 802-816 (1986), which is hereby incorporated by reference in its entirety.

A radiolabeled antibody of the present invention can be used for in vitro diagnostic tests. The specific activity of a tagged antibody, or binding portion thereof, depends upon the half-life, the isotopic purity of the radioactive label, and how the label is incorporated into the antibody. Table 1 lists several commonly-used isotopes, their specific activities, and half-lives. In immunoassay tests, the higher the specific activity, in general, the better the sensitivity.

TABLE 1

| Isotope | Isotope (Curies/Mole) | Half-Life |
| --- | --- | --- |
| 14C | $6.25 \times 10^1$ | 5720 years |
| 3H | $2.01 \times 10^4$ | 12.5 years |
| 35S | $1.50 \times 10^6$ | 87 days |
| 125I | $2.18 \times 10^6$ | 60 days |
| 32P | $3.16 \times 10^6$ | 14.3 days |
| 131I | $1.62 \times 10^7$ | 8.1 days |

Procedures for labeling antibodies with the radioactive isotopes listed in Table 1 are generally known in the art. Tritium labeling procedures are described in U.S. Pat. No. 4,302,438, to Zech, which is hereby incorporated by reference in its entirety. Iodinating, tritium labeling, and $^{35}$S labeling procedures especially adapted for murine monoclonal antibodies are described by Goding, *Monoclonal Antibodies: Principles and Practice*, pp. 124-126 (N.Y. Academic Press, 1983) and the references cited therein, which is hereby incorporated by reference in its entirety. Other procedures for iodinating antibodies, or binding portions thereof, are described by Hunter et al., *Nature* 144:945 (1962), David et al., *Biochemistry* 13:1014-1021 (1974), and U.S. Pat. Nos. 3,867,517 and 4,376,110, which are hereby incorporated by reference in their entirety. Radiolabeling elements which are useful in imaging include $^{123}$I, $^{131}$I, $^{111}$In, and $^{99m}$Tc, for example. Procedures for iodinating antibodies are described by Greenwood et al., *Biochem. J.* 89:114-123 (1963); Marchalonis, *Biochem. J.* 113:299-305 (1969); and Morrison et al., *Immunochemistry* 8:289-297 (1971), which are hereby incorporated by reference in their entirety. Procedures for $^{99m}$Tc-labeling are described by Rhodes et al., in Burchiel et al. (eds.), *Tumor Imaging: The Radioimmunochemical Detection of Cancer*, New York: Masson 111-123 (1982), and the references cited therein, which is hereby incorporated by reference in its entirety. Procedures suitable for $^{111}$In-labeling antibodies are described by Hnatowich et al., *J. Immul. Methods* 65:147-157 (1983), Hnatowich et al., *J. Applied Radiation* 35:554-557 (1984), and Buckley et al., *F.E.B.S.* 166:202-204 (1984), which are hereby incorporated by reference in their entirety.

A radiolabeled antibody is useful for administration to a patient, as described in more detail infra, because it may be detected or "imaged" in vivo using known techniques such as radionuclear scanning using e.g., a gamma camera or emission tomography. See e.g., Bradwell et al., "Developments in Antibody Imaging", *Monoclonal Antibodies for Cancer Detection and Therapy*, Baldwin et al., (eds.), pp. 65-85 (Academic Press 1985), which is hereby incorporated by reference in its entirety. Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Fluorophore and chromophore labeled antibodies can be prepared from standard moieties known in the art. Since antibodies and other proteins absorb light having wavelengths of up to about 310 nm, the fluorescent moieties should be selected to have substantial absorption at wavelengths above 310 nm and preferably above 400 nm. A variety of suitable fluorescers and chromophores are described by Stryer, *Science* 162:526 (1968) and Brand et al., *Annual Review of Biochemistry* 41:843-868 (1972), which are hereby incorporated by reference in their entirety. The antibodies can be labeled with fluorescent chromophore groups by conventional procedures such as those disclosed in U.S. Pat. Nos. 3,940,475, 4,289,747, and 4,376,110, which are hereby incorporated by reference in their entirety.

One group of fluorescers having a number of the desirable properties described supra are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies can be labeled with fluorchromes or chromophores by the procedures described by Goding, *Monoclonal Antibodies: Principles and Practice*, pp. 208-249 (N.Y. Academic Press, 1983), which is hereby incorporated by reference in its entirety. The antibodies can be labeled with an indicating group containing the NMR-active $^{19}$F atom, or a plurality of such atoms inasmuch as (i) substantially all of the naturally abundant fluorine atoms are the $^{19}$F isotope and, thus, substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described by Pykett, *Scientific American* 246:78-88 (1982), which is hereby incorporated by reference in its entirety.

A further aspect of the present invention relates to a kit for detecting phosphorylation of a prenyl-electrostatic switch in a K-Ras4B protein. The kit includes an isolated antibody which binds to a phosphorylated prenyl-electrostatic switch in a K-Ras4B protein where the antibody is bound to a label, and a device to detect the label.

Labels to which the antibody of the kit of the present invention may be bound are described supra. Devices to detect the label include, without limitation, in vitro and in vivo detection devices as described infra.

Another aspect of the present invention relates to a method of detecting phosphorylation of a prenyl-electrostatic switch on a GTPase protein in a biological sample. This method involves providing an antibody which binds to a phosphorylated prenyl-electrostatic switch on a K-Ras4B protein. The antibody is contacted with the biological sample. Binding that occurs between the biological sample and the antibody is detected to identify phosphorylation of a prenyl-electrostatic switch on the GTPase protein.

In a preferred embodiment, the GTPase protein is K-Ras4B protein, and the antibody has a label (described supra) to permit detection of binding of the antibody to a biological sample.

Detection of binding between the biological sample and the antibody of the present invention is carried out using an assay selected from the group consisting of a Western blot, immunoassay, ELISA assay, flow cytometry, radiography, and immunoscintography.

The antibody or binding portion thereof of the present invention may be administered to a subject, preferably a human. Administering may be carried out orally, parenterally, subcutaneously, intravenously, intramuscularly, intraperitoneally, by intravesical instillation, by intracavitary, intravesical instillation, intraocularly, intraarterially, intralesionally, or by application to mucous membrane.

When administered to a subject, detection of phosphorylation of a prenyl-electrostatic switch on a K-Ras4B protein is carried out using an in vivo detection method, which may include, without limitation, diagnostic imaging, ultrasound, tomography, magnetic resonance, elastography, and radionuclear scanning.

The detection method of the present invention may be utilized to evaluate efficacy of a cancer therapy in a subject, such as a human. Alternatively, the detection methods of the present invention may be utilized to evaluate progression of cancer state in a subject, such as a human.

EXAMPLES

The following examples are provided to illustrate embodiments of the present invention but are by no means intended to limit its scope.

Example 1

Plasmids

The full or partial coding sequences of the relevant human cDNAs were amplified by PCR and cloned in frame into pEGFP-C3, pECFP-C1, pYFP-C1 (Clontech, Palo Alto, Calif.), or pCGN-HA as indicated. Point mutants within the K-Ras C-terminus were generated by site-directed mutagenesis using the Quickchange XL Kit (Stratagene, La Jolla, Calif.). To construct pCGN-HA-RBD-PKCcat cDNAs, encoding residues 55-131 of Raf-1 and residues 383-707 of PKCθ were amplified by PCR and ligated in frame into pCGN-HA. All constructs were verified by bidirectional sequencing. To construct pEYFP-K-Ras12V-tailBcl-XL (YFP-K-Ras12V-tXL) and pEYFP-K-Ras12V-tailH-Ras (YFP-K-Ras12V-tH) encoding a fusion between K-Ras12V and the C-terminal 29 amino acids of Bcl-XL or 19 amino acids of H-Ras, respectively, cDNA encoding residues 204-233 of Bcl-XL, or residues 270-289 of H-Ras were amplified with appropriate overhangs and ligated in frame into the 3' linker of pEYFP-K-Ras12V followed by site-directed mutagenesis of the K-Ras12V stop codon.

Example 2

Cell Culture and Transfection

COS-1, HeLa, and MDCK cells were maintained in 5% $CO_2$ in Dulbecco's Modified Eagle Medium ("DMEM") supplemented with 4 mM 1-glutamine, 1.5 g/L sodium bicarbonate, 4.5 g/L glucose, and 10% fetal bovine serum ("FBS") (Cellgro®). MDCK cells stably expressing GFP-K-Ras or GFP-H-Ras were selected in G418 and sorted by FACS to yield cell lines expressing relatively low levels of the fluorescent Ras proteins (1-3 fold endogenous by immunoblots). NIH 3T3 cells were maintained in 10% $CO_2$ in DMEM supplemented with 4 mM 1-glutamine, 1.5 g/L sodium bicarbonate, 4.5 g/L glucose, and 10% calf serum (Colorado Serum Co., Denver, Colo.). Jurkat T cells were maintained in 5% $CO_2$ in RPMI containing 10% FBS. Cells to be examined by fluorescence microscopy were seeded at $2 \times 10^5$ per plate into 35 mm dishes containing a glass coverslip-sealed 15 mm cutout (MatTek, Ashland, Mass.) and transfected the next day using Lipofectamine (Invitrogen, Carlsbad, Calif.; NIH 3T3), Lipofectamine 2000 (Invitrogen, Carlsbad, Calif.; COS-1, HeLa, MDCK), or DMRIE (Invitrogen, Carlsbad, Calif.; Jurkat), according to the manufacturers' instructions. To ensure co-transfection of untagged cDNAs and fluorescent constructs, a DNA ratio of at least 5:1 (untagged:fluorescent) was used.

Example 3

Cell Stimulation and Imaging

Cells were stimulated while under continuous observation by adding 100 nM bryostatin-1 (Biomol), 100 nM PMA with or without 500 ng/ml Ionomycin, or 5 ng/ml anti-CD3 to 35 mm MatTek plates maintained at 37° C. using a PDMI-2 microincubator (Harvard Apparatus, Holliston, Mass.). Treatment of cells with 100 nM Ro 31-8220 (Biomol, Plymouth Meeting, Pa.) or 15 μg/ml W-13 Hydrochloride (EMD Biosciences, San Diego, Calif.) was initiated 10 min prior to stimulations. Where indicated, 25 pM MitoTracker Red CMXRos (Molecular Probes, Eugene, Oreg.) was added 10 min prior to stimulation. Living cells were imaged with a Zeiss 510 inverted laser scanning confocal microscope ("LSM"). A minimum of five 0.45 μM Z slices were acquired for each cell at each time point and representative images were chosen to display both plasma membrane and endomembranes. Fluorescence resonance energy transfer ("FRET") on mitochondria between CFP-K-Ras and YFP-Bcl-XL was detected by bleaching the acceptor (YFP-Bcl-XL) on individual mitochondria and measuring the increase in CFP emission intensity as quenching was released. FRET efficiency was calculated as $[I_{CFP(post-bleach)} - I_{CFP(pre-bleach)}]/I_{CFP(post-bleach)}$. TIFF images were processed with Adobe Photoshop 7.0.

Example 4

Metabolic Labeling

Twenty-four hours after transfection with various K-Ras constructs, COS-1 cells were pre-incubated at 37° C. for 4 hours in phosphate-free DMEM containing 10% dialyzed fetal calf serum ("FCS"). The medium was then replaced with phosphate-free DMEM containing 2 mCi of [$^{32}$P]orthophosphate. After 6 hours of labeling, the cells were stimulated with 100 nM bryostatin-1 for 20 min at 37° C. Jurkat cells were rinsed three times with prewarmed phosphate-free DMEM, and then incubated at 37° C. for 6 hours in phosphate-free DMEM containing 10% FBS (3:1 undialyzed:dialyzed) and 0.5 mCi/ml [$^{32}$P]orthophosphate. After incubation, the $^{32}$P-labeled cells were rinsed with prewarmed phosphate-free DMEM, and then stimulated with either anti-CD3 (10 μg/ml) or vehicle control for 30 min at 37° C. Both types of cells were then lysed in RIPA buffer containing protease inhibitors (Roche, Basel, Switzerland) and 10 μM microcystin and 5 mM NaF. K-Ras was immunoprecipitated using agarose conjugated with Y13-259 monoclonal anti-Ras antibody (Santa Cruz Biotechnology, Inc., Santa Cruz, Calif.), analyzed by SDS-PAGE and visualized by phosphorimager.

Example 5

Immunogold Electron Microscopy

Jurkat cells (in suspension) were treated with 100 nM bryostatin-1 or vehicle (dimethyl sulfoxide ("DMSO")) for 30 minutes at 37° C. and then fixed with 2% formaldehyde and 0.2% glutaraldehyde in 0.1 M sodium phosphate buffer, pH 7.4. After washing in buffer, the cells were pelleted by centrifugation, embedded in 10% gelatin, cooled in ice, and cut into 1-mm$^3$ blocks in the cold room. The blocks were infused with 2.3 M sucrose at 4° C. for at least 2 hours, frozen in liquid nitrogen, and stored until cryo-ultramicrotomy. 100-nm-thick section were cut at −120° C. using an Ultracut T/FCS (Leica) equipped with an antistatic device (Diatome) and a diamond knife (Drukker). Ultrathin sections were picked up in a mix of 1.8% methylcellulose and 2.3 M sucrose (1:1) (Liou et al., "Improving Structural Integrity of Cryosections for Immunogold Labeling," *Histochemistry and Cell Biology* 106:41-58 (1996), which is hereby incorporated by reference in its entirety). Cryosections were collected on formvar-coated copper grids and incubated with Ras10 monoclonal antibody (Upstate, Charlottesville, Va.) followed by rabbit anti-mouse antibodies and then protein A gold (Slot et al., "A New Method of Preparing Gold Probes for Multiple-Labeling Cytochemistry," *Eur. J. Cell. Biol.* 38:87-93 (1985), which is hereby incorporated by reference in its entirety). After labeling, the sections were treated with 1% glutaraldehyde, counterstained with uranyl acetate, and embedded in methyl cellulose-uranyl acetate (Slot et al., "Immuno-Localization of the Insulin Regulatable Glucose Transporter in Brown Adipose Tissue of the Rat," *J. Cell. Biol.* 113:123-135 (1991), which is hereby incorporated by reference in its entirety). Images were acquired with a JEOL electron microscope JEM-1200 EX II at 80 kV.

Example 6

Caspase 3 Activation

The assay was performed as described (Vos et al., "The Pro-Apoptotic Ras Effector Nore1 May Serve as a Ras-Regulated Tumor Suppressor in the Lung," *J. Biol. Chem.* 278: 21938-21943 (2003), which is hereby incorporated by reference in its entirety). COS-1 cells were co-transfected with plasmids encoding the YFP-caspase 3 activation sensor (Clontech, Palo Alto, Calif.) and either vector or the indicated Ras construct. Twenty-four hours later the cells were imaged alive by LSM and 6-10 random, low-power fields were acquired. Nuclear accumulation or exclusion of the sensor was scored for each cell in each field post-acquisition, and the apoptotic index was calculated as the percent of cells with nuclear accumulation of the probe.

Example 7

Co-Immunoprecipitation

Cos-1 cells were co-transfected with GFP-tagged Bcl-2, Bcl-XL, Bak, Bax, or Bid, and either HA-tagged K-Ras12V or 12V181E constructs. Twenty-four hours later the cells were lysed and Ras was immunoprecipitated with Y13-259 rat monoclonal pan-Ras antibody. Immunoprecipitates were analyzed in duplicate by immunoblot with either Ras10 anti-Ras monoclonal antibody or anti-GFP polyclonal anitiserum followed by [$^{125}$I]protein A. Immunoprecipitated proteins were quantified by PhosphorImager. The amount of co-immunoprecipitated GFP-tagged Bcl-2 family member protein was normalized to the amount of immunoprecipitated HA-K-Ras. The lysates were analyzed by immunoblot to assure equal expression.

Example 8

Soft Agar Assays

NIH 3T3 cells stably transfected with pCGN-hyg, or the same vector encoding K-Ras12V or K-Ras12V 181 A were plated as single cell suspensions (2×10$^4$ cells/35-mm well) in 0.4% agar over a bottom layer of 0.6% agar, both containing DMSO vehicle or various concentrations of bryostatin-1. After two weeks, the percentage of plated cells that formed colonies (>5 cell diameters across) was determined.

Example 9

Tumor Growth Assays

NIH 3T3 cells stably transfected as per the soft agar assays were injected (5×10$^5$ cells) subcutaneously into the flanks of 4-6 week old athymic nude BALB/c mice. After formation of palpable tumors, mice were treated daily for 3 days with intraperitoneal DMSO vehicle or bryostatin-1 (25 μg/kg). Tumor volume was measured daily and differences in growth rates were evaluated for statistical significance by ANOVA.

Example 10

PKC Agonists Modulate the Association of K-Ras with the Plasma Membrane

K-Ras, tagged with green fluorescent protein ("GFP"), was expressed in a variety of cell types and its subcellular localization was observed in individual living cells before and after stimulation of PKC with bryostatin-1, a potent agonist that, like phorbol esters, binds to the C1 regulatory domains of PKCs and promotes their association with membranes (Kortmansky et al., "Bryostatin-1: A Novel PKC Inhibitor in Clinical Development," *Cancer Invest.* 21:924-936 (2003), which is hereby incorporated by reference in its entirety). Before stimulation, GFP-K-Ras was observed almost exclusively on the plasma membrane. Bryostatin-1 induced a rapid (<1 min onset, 3 min maximal) translocation of the GTPase from the plasma membrane to intracellular membranes (FIG. 1B). Phorbol myristate acetate ("PMA") had a similar but much weaker effect, consistent with its lower potency relative to bryostatin-1 (Szallasi et al., "Differential Regulation of Protein Kinase C Isozymes by Bryostatin 1 and Phorbol 12-Myristate 13-Acetate in NIH 3T3 Fibroblasts," *J. Biol. Chem.* 269:2118-2124 (1994), which is hereby incorporated by reference in its entirety). However, when PMA was combined with the calcium ionophore ionomycin, known to synergize with PMA in stimulating PKCs, the effects on GFP-K-Ras localization were identical to those of bryostatin-1 (FIG. 1C). GFP, extended with the 20 amino acid C-terminal region of K-Ras, behaved in a manner identical to that of full length GFP-K-Ras, demonstrating that all of the information required for both plasma membrane targeting and translocation in response to PKC activation was contained in this region. Neither H-Ras, an isoform lacking a polybasic region, nor Rac1, a Ras-related GTPase with a polybasic region devoid of phosphorylation sites (FIG. 1A), was redistributed in response to PKC agonists (FIG. 1B). The localization of K-Ras extended beyond its CAAX sequence with the hypervariable region of H-Ras was also unaffected by PKC agonists (FIG. 1B), demonstrating that the H-Ras membrane anchor is dominant when placed in tandem with the K-Ras polybasic region. The effect of bryostatin-1 on K-Ras localization was reversible (FIG. 1D) consistent with a phosphorylation/dephosphorylation cycle, a conclusion also supported by the observation that the phosphatase inhibitor, okadaic acid, induced partial internalization of GFP-K-Ras. Thus, PKC agonists dynamically regulate the association of K-Ras with the plasma membrane via its C-terminal segment.

Example 11

PKC-Mediated Phosphorylation of K-Ras on Serine 181 Promotes K-Ras Internalization The synergistic effect of ionomycin on PMA induced K-Ras translocation raised the possibility that calcium might play a role beyond the activation of PKCs since calmodulin has been shown to associate with (Villalonga et al., "Calmodulin Binds to K-Ras, But not to H- or N-Ras, and Modulates Its Downstream Signaling," *Mol. Cell. Biol.* 21:7345-7354 (2001), which is hereby incorporated by reference in its entirety) and extract (Sidhu et al., "Ca2+/Calmodulin Binds and Dissociates K-RasB from Membrane," *Biochem. Biophys. Res. Commun.* 304:655-660 (2003), which is hereby incorporated by reference in its entirety) K-Ras from membrane fractions in vitro, a process antagonized by calmodulin inhibitors. Although bryostatin-1 is not known to mobilize intracellular calcium suggesting that PKC activation is sufficient for K-Ras translocation, the role of calmodulin was nevertheless tested. Pharmacologic inhibition of calmodulin affected neither PMA+Iono nor bryostatin-1 stimulated translocation of K-Ras (FIG. 2A), suggesting that calmodulin does not play a role. In contrast, the PKC inhibitor Ro 31-8220 completely blocked K-Ras translocation (FIG. 2A).

Although the effects of PKC activation on K-Ras localization could be indirect, the previous demonstration of a PKC substrate in the C-terminus of K-Ras (Ballester et al., "Phorbol Ester- and Protein Kinase C-Mediated Phosphorylation of the Cellular Kirsten Ras Gene Product," *J. Biol. Chem.* 262:2688-2695 (1987), which is hereby incorporated by reference in its entirety) suggested that the effect is more likely direct. The C-terminal region of K-Ras harbors three potential phosphate acceptors, S171, S181, and T183 (FIG. 1A), although only the serines conform to consensus phosphorylation sites and previous phospho-amino acid analysis of K-Ras from cells exposed to PKC agonists revealed only phosphoserine (Ballester et al., "Phorbol Ester- and Protein Kinase C-Mediated Phosphorylation of the Cellular Kirsten Ras Gene Product," *J. Biol. Chem.* 262:2688-2695 (1987), which is hereby incorporated by reference in its entirety). Sequence analysis revealed that within the C-terminal membrane-anchoring region of K-Ras, S181 conforms most closely to a consensus PKC site. Whereas substitution of alanine for serine at position 181 completely blocked bryostatin-1 induced translocation of GFP-K-Ras, double substitution of S171 and T183 for alanines did not inhibit K-Ras internalization (FIG. 2A). Substitution of glutamic acid for S181 to create a phosphomimetic residue resulted in a form of K-Ras that was constitutively associated with internal membranes (FIG. 2A). These data suggest that K-Ras is a direct substrate for PKC and that phosphorylation of S181 mediates translocation.

To confirm phosphorylation of S181 of K-Ras metabolic labeling was performed with [$^{32}$P]orthophosphate of cells expressing various K-Ras mutants. Bryostatin-1 induced phosphorylation of K-Ras that was markedly diminished with an S181A substitution, confirming S181 as the major phosphate acceptor (FIG. 2B). However, the low level of $^{32}$P incorporation into the 181A mutant suggests that, although S181 is the primary site, other minor sites of phosphorylation are likely. The diminished signal in the S171A mutant suggested that this residue may also serve as a phosphate acceptor. In contrast, a T183A substitution did not diminish $^{32}$P incorporation confirming that phosphorylation of this residue is not involved in regulating K-Ras localization. Phosphomimetic (glutamic acid) substitution of S171 resulted in some constitutive internalization, although substitution of S181 was more efficient in this regard and a double mutant, GFP-KRas12V171E181E, was indistinguishable from GFP-K-Ras12V181E. Together these data suggest that whereas reversible phosphorylation of S181 is both necessary and sufficient to cause K-Ras translocation, phosphorylation of S171 may also contribute.

The sufficiency of a single phosphorylation event for discharge of K-Ras from the plasma membrane suggested that the basal affinity for the plasma membrane imparted by the polybasic region is relatively low. To test this idea, cells were metabolically labeled with [$^{35}$S]methionine and tracked by subcellular fractionation and immunoprecipitation, the localization of GFP-K-Ras stably expressed at a level equivalent to the endogenous protein. After steady-state labeling (17 hrs) 23.8±6.8% (mean±SEM, n=3) of GFP-K-Ras was recovered in the S100. Moreover, when the P100 was re-homogenized with unlabeled, isotonic cytosol and then recovered by centrifugation, 39±5% (mean±SEM, n=4) was recovered in the high speed supernatant. These data suggest that the binding affinity of K-Ras for membranes is relatively low and that merely a partial neutralization of the polybasic region could be sufficient to significantly affect the overall membrane affinity.

If bryostatin-1 induces internalization of K-Ras via recruitment and activation of PKC at the plasma membrane where K-Ras resides, then targeting PKC to K-Ras in a bryostatin-independent fashion should promote constitutive internalization. To test this idea, the catalytic domain of PKCO fused with the Ras binding domain (RBD) of Raf-1 was expressed and it was found that, in cells expressing this construct, GFP-K-RasV12 with a wild type C-terminus was partially internalized but GFP-K-Ras12V181A was not (FIG. 2C). This result confirms that S181 is a PKC site and that its phosphorylation is necessary and sufficient for PKC induced translocation of K-Ras to internal membranes. These data suggest that PKC regulates the subcellular localization of K-Ras via a farnesyl-electrostatic switch. Evolutionarily conserved, consensus phosphorylation sites analogous to S181 of K-Ras are also found in Ras-related proteins of both the Ras and Rho families, suggesting that a prenyl-electrostatic switch may be a general mechanism for a subclass of GTPases (FIG. 2D). Indeed, phosphorylation of these sites in Rap1a (Lerosey et al., "The cAMP-Dependent Protein Kinase Phosphorylates the Rap1 protein In Vitro as well as in Intact Fibroblasts, but not the Closely Related Rap2 Protein," *Biochem. Biophys. Res. Commun.* 175:430-436 (1991); Quilliam et al., "Rap1A is a Substrate for Cyclic AMP-Dependent Protein Kinase in Human Neutrophils," *J. Immunol.* 147:1628-1635 (1991), which are hereby incorporated by reference in their entirety) and RhoA (Lang et al., "Protein Kinase A Phosphorylation of RhoA Mediates the Morphological and Functional Effects of Cyclic AMP in Cytotoxic Lymphocytes," *EMBO J.* 15:510-519 (1996), which is hereby incorporated by reference in its entirety) has been reported. Moreover, it has been observed that PKC dependent Rnd3 translocation from the plasma membrane to internal membranes that can be mimicked by substituting a negatively charged residue for the Rnd3 serine at the position analogous to S181 of K-Ras.

Example 12

T Cell Signaling Induces K-Ras Internalization and Ras Phosphorylation

To verify that the effect observed by direct activation of PKC with diacylglycerol analogs reflected physiologic signaling, lymphocytes that are well known to activate both Ras (Downward et al., "Stimulation of p21ras Upon R-Cell Activation," *Nature* 346:719-723 (1990), which is hereby incorporated by reference in its entirety) and PKC (Valge et al., Protein Kinase C is Required for Responses to T Cell Receptor Ligands but not to Interleukin-2 in T Cells," *Cell* 55:101-112 (1988), which is hereby incorporated by reference in its entirety) were studied following engagement of the T cell receptor. GFP-K-Ras expressed on the plasma membrane of Jurkat T cells was observed in 50% of cells to rapidly (<5 min) translocate to internal membranes in response to crosslinking of the T cell receptor with anti-CD3 antibodies (FIG. 2E). Phosphorylation of endogenous Ras was observed in Jurkat T cells following stimulation of the T cell receptor (FIG. 2F), demonstrating Ras phosphorylation in response to physiological signaling.

Example 13

PKC Induces Translocation of K-Ras from the Plasma Membrane to Endoplasinic Reticulum, Golgi Apparatus, and Mitochondria Because farnesylated K-Ras that lacks a polybasic sequence in the C-terminal hypervariable region localizes on the endoplasmic reticulum and Golgi apparatus (Choy et al., "Endomembrane Trafficking of Ras: The CAAX Motif Targets Proteins to the ER and Golgi," *Cell* 98:69-80 (1999), which is hereby incorporated by reference in its entirety), it was predicted that these would be the intracellular compartments upon which phosphorylated K-Ras accumulates. Indeed, the clear decoration of the nuclear envelope with GFP-K-Ras in cells treated with bryostatin-1 identified the endoplasmic reticulum as one target compartment (FIGS. 1B and 2A). This was confirmed by colocalization of YFP-K-Ras with a CFP-tagged endoplasmic reticulum marker in bryostatin-1 treated cells (FIG. 3A). Similarly, association with the Golgi apparatus was demonstrated with a CFP-tagged Golgi marker (FIG. 3A). However, the endoplasmic reticulum and Golgi localization did not account for all of the internalized K-Ras. Also apparent were widely scattered structures that had a vesicular appearance. Unexpectedly, these structures proved to be mitochondria as demonstrated by colocalization with MitoTracker Red (FIG. 3A). The fluorescence pattern around the rim of mitochondria marked by MitoTracker Red suggested localization on the outer mitochondrial membrane (FIG. 3A, inset). To rule out the possibility that the mitochondrial localization was a function of GFP-K-Ras overexpression, MDCK cell lines that stably express GFP-K-Ras or GFP-H-Ras at endogenous levels were examined. As in the transiently transfected cells, bryostatin-1 stimulated rapid association of GFP-K-Ras but not GFP-H-Ras with mitochondria (FIG. 3B).

To determine if endogenous Ras localizes on mitochondria in a PKC dependent fashion, immunogold EM studies were performed on Jurkat T cells (FIG. 3C). In untreated cells, 6.4±0.5 (mean±SEM, n=8) 10 nm gold particles/μm2 of cytoplasm (excluding plasma membrane) were observed, of which less than 1 in 3 were associated with mitochondria. In bryostatin-1 treated cells, 31.0±1.1 gold particles/$\mu m^2$ were observed, of which 49% were associated with mitochondria and the rest with endoplasmic reticullum, Golgi, and nuclear envelope. Of the mitochondria associated gold particles in bryostatin-1 treated cells, 81% were located within 30 nm of the outer mitochondrial membrane, confirming the fluorescence results and demonstrating PKC dependent association of endogenous Ras with mitochondria. Although the only antibody that proved useful in the immunogold EM study was a pan-Ras antibody, the fluorescent studies strongly suggest that the endogenous Ras observed on mitochondria was K-Ras.

Example 14

Phosphorylated K-Ras Promotes Apoptosis

It has been shown that Ras proteins can signal from endomembrane (Bivona et al., "Phospholipase Cgamma Activates Ras on the Golgi Apparatus by Means of RasGRP1," *Nature* 424:694-698 (2003); Chiu et al., "Ras Signalling on the Endoplasmic Reticulum and the Golgi," *Nat. Cell. Biol.* 4:343-350 (2002), which are hereby incorporated by reference in their entirety). Accordingly, the signaling characteristics of K-Ras internalized via its farnesyl-electrostatic switch was determined. The protean effects of PKC agonists on signaling pathways make interpretation of experiments utilizing these agents difficult. Therefore, it was sought to specifically determine the effects of phosphorylation of S181 on K-Ras signaling by expressing phosphomimetic K-Ras12V181E and to test its function. However, this approach proved impracticable because of the surprising observation that expression of K-Ras12V181E was highly toxic to cells. Ras proteins have been found to regulate both anti- and pro-apoptotic signaling (Cox and Der, "The Dark Side of Ras: Regulation of Apoptosis," *Oncogene* 22:8999-9006 (2003), which is hereby incorporated by reference in its entirety). Therefore, the possibility that the observed toxicity was a result of apoptosis was tested. Overexpression of Bcl-2

(FIG. 4A) or a caspase 3/7 inhibitor blocked the toxicity of K-Ras12V181E, implicating apoptosis.

To confirm that K-Ras phosphorylated at S181 could induce apoptosis, a YFP-tagged caspase 3 sensor was utilized, which localizes in the cytosol of healthy cells, but enters the nucleus of cells undergoing apoptosis (yos et al., "RASSF2 is a Novel K-Ras Specific Effector and Potential Tumor Suppressor," *J. Biol. Chem.* 278:28045-28051 (2003), which is hereby incorporated by reference in its entirety). Exposure of COS-1 cells to UV light induced translocation of the caspase sensor into the nucleus (FIG. 4B). UV exposure of cells expressing GFP-K-Ras induced apoptosis but did not induce internalization of the GTPase, demonstrating that internalization of K-Ras is not a general consequence of apoptosis. Expression of activated H-Ras61L resulted in a relatively low apoptotic index similar to that of vector transfected cells (FIGS. 4B and 4C). In contrast, overexpression of K-Ras12V resulted in a slightly elevated apoptotic index. Importantly, expression of K-Ras12V181E but not K-Ras12V181 A induced a high degree of apoptosis (FIGS. 4B and 4C). K-Ras17N181E, predicted to be nucleotide free and therefore incapable of interacting with effectors, was inactive in the apoptosis assay demonstrating a GTP-dependence (FIG. 4C). Co-expression of the Raf-1 RBD with K-Ras12V181E blocked apoptosis, confirming that cell death was mediated through the effector-binding domain of K-Ras12V181E. K-Ras mutants in which the C-terminal polylysine sequence is changed to uncharged polyglutamine localize on the endoplasmic reticulum and Golgi but not mitochondria and do not affect cell viability (Choy et al., "Endomembrane Trafficking of Ras: The CAAX Motif Targets Proteins to the ER and Golgi," *Cell* 98:69-80 (1999); Hancock et al., "A Polybasic Domain or Palmitoylation is Required in Addition to the CAAX Motif to Localize p21$^{ras}$ to the Plasma Membrane," *Cell* 63:133-139 (1990), which are hereby incorporated by reference in their entirety). Together, these data suggest that relocalization of K-Ras from the plasma membrane to the mitochondria stimulates apoptosis via a GTP-dependent interaction on that organelle.

To confirm that K-Ras12V phosphorylated on S181, like phosphomimetic K-Ras12V181E, is pro-apoptotic, the capacity of PKC agonists to induce apoptosis of K-Ras transformed fibroblasts was examined. Both bryostatin-1 (FIG. 4D) and PMA plus ionomycin induced apoptosis to a much higher extent in cells transformed with K-Ras12V than those transformed with K-Ras12V181A. Thus, the sensitization to PKC-mediated apoptosis afforded by K-Ras transformation can be attributed to phosphorylation at S181.

Example 15

K-Ras Interacts with Bcl-XL on Mitochondria

Mounting evidence in recent years strongly suggests that Ras can have pro-apoptotic effects in some cellular contexts (Cox and Der, "The Dark Side of Ras: Regulation of Apoptosis," *Oncogene* 22:8999-9006 (2003); Downward, "Ras Signalling and Apoptosis," *Curr. Opin. Genet. Dev.* 8:49-54 (1998), which are hereby incorporated by reference in their entirety). The most compelling evidence has come from the characterization of a family of tumor suppressors that promote apoptosis and that have proven to be Ras effectors. The best-characterized of these is Norel (Khokhlatchev et al., "Identification of a Novel Ras-Regulated Proapoptotic Pathway," *Curr. Biol.* 12:253-265 (2002), which is hereby incorporated by reference in its entirety). A dominant negative form of Norel (Khokhlatchev et al., "Identification of a Novel Ras-Regulated Proapoptotic Pathway," *Curr. Biol.* 12:253-265 (2002), which is hereby incorporated by reference in its entirety) had no effect on the ability of K-Ras12V181E to induce apoptosis, suggesting that phosphorylated K-Ras induces cell death via a Norel-independent pathway.

Apoptosis can be mediated from intrinsic cellular pathways that originate from the endoplasmic reticulum and mitochondria (Breckenridge et al., "Regulation of Apoptosis by Endoplasmic Reticulum Pathways," *Oncogene* 22:8608-8618 (2003), which is hereby incorporated by reference in its entirety). Thus, the intracellular localizations of phosphorylated K-Ras include the cytoplasmic face of organelles intimately associated with apoptosis. The Bcl-2 family of proteins regulates the permeability transition of the outer mitochondrial membrane that characterizes apoptosis. Ras has been reported to interact with Bcl-2 (Rebollo et al., "Bcl-2 Differentially Targets K-, N-, and H-Ras to Mitochondria in IL-2 Supplemented or Deprived Cells: Implications in Prevention of Apoptosis," *Oncogene* 18:4930-4939 (1999), which is hereby incorporated by reference in its entirety) suggesting that direct interaction with Bcl-2 or related proteins could mediate the pro-apoptotic affects of phosphorylated K-Ras. The capacity of K-Ras to associate with various Bcl-2 family proteins (Bcl-2, Bcl-XL, Bak, Bax, and Bid) was examined by co-immunoprecipitation. Although association with Bcl-2 was confirmed, this interaction was insensitive to PKC agonists. In contrast, it was observed that K-Ras associated with Bcl-XL in a PKC-dependent fashion. Moreover, K-Ras12V181E brought down 6.8±2.3 fold (n=10, p<0.04) more Bcl-XL than did K-Ras12V. To determine the compartment upon which K-Ras and Bcl-XL interact, cells expressing CFP-K-Ras12V and YFP-Bcl-XL were examined before and after stimulation with PKC agonists (FIG. 5). YFP-Bcl-XT was observed constitutively on the outer mitochondrial membrane and CFP-K-Ras12V colocalized with YFP-Bcl-XL on that compartment following treatment with bryostatin-1 (FIG. 5A) or PMA plus ionomycin (FIG. 5B). To determine if this colocalization reflected an in vivo molecular interaction, fluorescence resonance energy transfer were measured between the two fluorophors. By selectively photobleaching the acceptor (YFP-Bcl-XL) on individual mitochondria and measuring a release of quenching of the donor (CFP-K-Ras), FRET with an efficiency of 17±8% was detected, establishing a PKC-dependent molecular interaction between K-Ras and Bcl-XL on the surface of mitochondria.

Example 16

Mitochondrial Targeted K-Ras Requires a Negative Charge at Position 181 to Promote Apoptosis To test the idea that localization of activated K-Ras on mitochondria would be sufficient to promote apoptosis, its native CAAX sequence was replaced with the C-terminal sequence of Bcl-XL that serves as an efficient outer mitochondrial membrane targeting sequence. A YFP-tagged version of this chimeric protein, YFP-K-Ras12VtXL, localized exclusively on mitochondria (FIG. 6A, upper panels). K-Ras targeted to the mitochondria in this fashion was disposed in such a way that it could interact with effectors, as evidenced by the recruitment of CFP-RBD to mitochondrial-associated YFP-K-Ras12VtXL (FIG. 5A, lower panels). CFP-K-Ras12VtXL expressed with the YFP-tagged caspase 3 sensor induced no more apoptosis than did CFP alone (FIG. 5B) demonstrating that mitochondrial localization of activated K-Ras alone was insufficient to promote apoptosis. When the equivalent of amino acid 181 in CFP-K-Ras12VtXL was changed to glutamic acid to mimic a phosphate residue, the construct (CFP-K-Ras12V181EtXL) acquired pro-apoptotic activity similar to that of CFP-K-Ras12V181E (FIG. 5B). Thus, K-Ras localized exclusively to the mitochondria can stimulate apoptosis provided it incorporates a negative charge at position S181.

Example 17

Bryostatin Inhibits K-Ras Driven Tumorigenesis in a S181 Dependent Manner

The results suggest that, by promoting apoptosis, phosphorylation of oncogenic K-Ras on S181 might reverse cellular transformation and/or tumor progression. To test this idea, the effect of bryostatin-1 on K-Ras-dependent transformation was studied in vitro and in vivo. Bryostatin-1 inhibited K-Ras12V induced colony growth of fibroblasts in soft agar (FIG. 7A). In contrast, soft agar growth induced by K-Ras12V181A was insensitive to bryostatin-1. Concordant with these in vitro results, tumors in nude mice established with fibroblasts transformed with K-Ras12V were sensitive to intraperitoneal administration of bryostatin-1 but tumors established with K-Ras12V181 A transformed fibroblasts were resistant (FIG. 7B). Thus, the K-Ras farnesyl-electrostatic switch inhibits tumor growth in vivo, consistent with its ability to promote programmed cell death. In phase I and II trials, bryostatin-1 exhibited clinical efficacy with minimal toxicity against a variety of tumors (Kortmansky et al., "Bryostatin-1: A Novel PKC Inhibitor in Clinical Development," *Cancer Invest.* 21:924-936 (2003), which is hereby incorporated by reference in its entirety). The results reveal a previously unsuspected mechanism by which bryostatin-1 exerts anti-neoplastic effects. Thus, agents selected to stimulate phosphorylation of K-Ras on S181 will have significant potential as novel anti-cancer therapeutics.

Peripheral membrane proteins have an advantage over transmembrane proteins in that their subcellular localization can be rapidly modulated. Many small GTPases take full advantage of this feature, moving on and off target membranes as part and parcel of their biological task. For example, many Rho family proteins cycle between membranes and their cytosolic chaperone, RhoGDI (Michaelson et al., "Differential Localization of Rho GTPases in Live Cells. Regulation by Hypervariable Regions and RhoGDI Binding," *J. Cell. Biol.* 152:111-126 (2001), which is hereby incorporated by reference in its entirety). Similarly, Rab (Seabra et al., "Controlling the Location and Activation of Rab GTPases," *Curr. Opin. Cell. Biol.* 16:451-457 (2004), which is hereby incorporated by reference in its entirety) and Arf (Beraud-Dufour et al., "Dual Interaction of ADP Ribosylation Factor 1 with Sec7 Domain and with Lipid Membranes During Catalysis of Guanine Nucleotide Exchange," *J. Biol. Chem.* 274:37629-37636 (1999), which is hereby incorporated by reference in its entirety) family proteins cycle on and off target membranes as part of their activation cycle. In contrast, mature Ras proteins were thought until recently to associate irreversibly with the plasma membrane, the compartment upon which they were thought to exclusively act. This view is somewhat counterintuitive since Ras proteins, unlike most Rho and Rab proteins, are modified with a single 15-carbon farnesyl lipid rather than one or two 20-carbon geranylgeranyl lipids and thereby have less intrinsic affinity for membranes. Indeed, it has recently been found that whereas reversible carboxyl methylation of the prenylcysteine is required for membrane association of Ras proteins, it is not required for Rho proteins (Michaelson et al., "Postprenylation CAAX Processing Is Required for Proper Localization of Ras but Not Rho GTPases," *Mol. Biol. Cell.* 16:1606-1616 (2005), which is hereby incorporated by reference in its entirety), suggesting that the shorter prenyl modification evolved to afford relatively weak and reversible affinity for membranes. It is now clear that the palmitoylated forms of Ras signal from endomembrane as well as the plasma membrane (Bivona et al., "Phospholipase Cgamma Activates Ras on the Golgi Apparatus by Means of RasGRP1," *Nature* 424: 694-698 (2003); Chiu et al., "Ras Signaling on the Endoplasmic Reticulum and the Golgi," *Nat. Cell. Biol.* 4:343-350 (2002), which are hereby incorporated by reference in their entirety) and that retrograde trafficking of these proteins from the plasma membrane to the Golgi is regulated by a palmitoylation/depalmitoylation cycle (Goodwin et al., "Depalmitoylated Ras Traffics to and from the Golgi Complex Via Non-Vesicular Pathway," *Journal of Cell Biology*, In Press (2005); Rocks et al., "An Acylation Cycle Regulates Localization and Activity of Palmitoylated Ras Isoforms," *Science* 307:1746-1752 (2005), which are hereby incorporated by reference in their entirety) demonstrating conclusively that the farnesyl membrane anchor is relatively weak. Thus, K-Ras is now added to the list of mature Ras proteins that can translocate between subcellular compartments. As has been previously shown for proteins such as MARCKS, the membrane affinity is modulated by phosphorylation within the polybasic region that serves to partially neutralize the charge and destabilize the electrostatic interaction with negatively charged phospholipid headgroups on the inner leaflet of the plasma membrane. This newly recognized feature of K-Ras is termed a farnesyl-electrostatic switch in analogy with the MARCKS myristoyl-electrostatic switch.

At first glance, the sufficiency of a single phosphorylation event to trigger the K-Ras farnesyl-electrostatic switch seemed surprising. It is often stated that MARCKS requires three phosphorylation events in the polybasic region to activate its myristoyl-electrostatic switch. However, there is no evidence for this. The only mutant evaluated in the literature for resistance to PKC stimulated translocation is one that incorporates alanine substitutions for each of three serines (Ohmori et al., "Importance of Protein Kinase C Targeting for the Phosphorylation of Its Substrate, Myristoylated Alanine-Rich C-Kinase Substrate," *J. Biol. Chem.* 275:26449-26457 (2000); Seykora et al., "Molecular Determinants of the Myristoyl-Electrostatic Switch of MARCKS," *J. Biol. Chem.* 271:18797-18802 (1996), which are hereby incorporated by reference in their entirety). The stoichiometry of PKC mediated MARCKS phosphorylation suggests that only one serine in the polybasic region may be phosphorylated (Kim et al., "Phosphorylation, High Ionic Strength, and Calmodulin Reverse the Binding of MARCKS to Phospholipid Vesicles," *J. Biol. Chem.* 269:28214-28219 (1994); McIlroy et al., "Phosphorylation-Dependent Binding of a Synthetic MARCKS Peptide to Calmodulin," *J. Biol. Chem.* 266:4959-4964 (1991), which are hereby incorporated by reference in their entirety). Regardless of the actual number of phosphoserines within the polybasic region of the MARCKS protein required for its dissociation from the plasma membrane, the analogy between MARCKS and K-Ras can be taken only so far. First of all, the acyl chain at the N-terminus of MARCKS will have a different membrane affinity than that of the branched and unsaturated polyisoprene at the C-terminus of K-Ras. Second, whereas the polybasic region of K-Ras is immediately adjacent to the lipid chain, that of the MARCKS protein is far removed. Most important, the polybasic region of MARCKS contains, in addition to the positively charged lysines, five conserved phenylalanines. Two-dimensional nuclear Overhauser enhancement spectroscopy NMR experiments showed that the aromatic rings of these phenylalanine residues penetrate into the acyl chain region of phosphatidylcholine bilayers (Zhang et al., "Binding of Peptides with Basic and Aromatic Residues to Bilayer Membranes: Phenylalanine in the Myristoylated Alanine-Rich C Kinase Substrate Effector Domain Penetrates into the Hydrophobic Core of the Bilayer," *J. Biol. Chem.* 278:21459-21466 (2003), which is hereby incorporated by reference in its entirety). This is predicted to increase dramatically the free energy of association. K-Ras has no such hydrophobic side chains in its polybasic region. Thus, the electrostatic repulsive force required to dislodge MARCKS is likely to be much greater than that for K-Ras.

The affinity of K-Ras for membranes in vitro is relatively weak. Seventy percent of GFP fused to a K-Ras tail could be extracted from cellular membranes with anionic phospholipid vesicles (Roy et al., "Mutational and Biochemical Analysis of Plasma Membrane Targeting Mediated by the Farnesylated, Polybasic Carboxy Terminus of K-Ras4B," *Biochemistry* 39:8298-8307 (2000), which is hereby incorporated by reference in its entirety). Similarly, 70% of K-Ras was extracted from membrane vesicles with 0.25 M salt (Hancock et al., "A Polybasic Domain or Palmitoylation is Required in Addition to the CAAX Motif to Localize p21$^{ras}$ to the Plasma Membrane," *Cell* 63:133-139 (1990), which is hereby incorporated by reference in its entirety). Substitution of glutamine for two of the six contiguous lysines, the electrostatic equivalent of adding a phosphate group, resulted in recovery of 34% of K-Ras in the soluble fraction (Hancock et al., "A Polybasic Domain or Palmitoylation is Required in Addition to the CAAX Motif to Localize p21$^{ras}$ to the Plasma Membrane," *Cell* 63:133-139 (1990), which is hereby incorporated by reference in its entirety). The data provided herein reveal that 40% of total K-Ras can be extracted from total membrane fractions with isotonic cytosol. These data suggest that even a partial neutralization of the overall charge of the K-Ras polybasic region may be sufficient to significantly affect membrane affinity. The relative effects of partial neutralization of the polybasic region with regard to membrane affinity will depend on the chemical composition of the target membrane. Reversible phosphorylation of S181 of K-Ras, although insufficient to neutralize the entire net positive charge of the region, provides sufficient neutralization to constitute a farnesyl-electrostatic switch that promotes dissociation of K-Ras from the plasma membrane but allows association with intracellular membranes. In this way, the endomembrane serves as a sink and thereby increases the apparent, in vivo dissociation constant for K-Ras at the plasma membrane.

The Golgi apparatus and endoplasmic reticulum localization of phosphorylated K-Ras was not surprising since K-Ras mutants with glutamines substituted for the lysines of the polybasic region were previously found on these compartments (Choy et al., "Endomembrane Trafficking of Ras: The CAAX Motif Targets Proteins to the ER and Golgi," *Cell* 98:69-80 (1999), which is hereby incorporated by reference in its entirety). The mitochondrial localization has not previously been observed in intact cells expressing GFP tagged Ras proteins. The basis for the affinity of phosphorylated K-Ras for the outer mitochondrial membrane may reflect the phospholipid content of this compartment or the presence of a specific acceptor. Alternatively, or in addition, the interaction demonstrated between phospho-K-Ras and Bcl-XL, a constitutive component of the outer mitochondrial membrane, may explain the affinity.

Although usually thought of as promoting cell growth and survival, the pro-apoptotic effects of Ras in some cellular contexts are well described (Cox et al., "The Dark Side of Ras: Regulation of Apoptosis, *Oncogene* 23:8999-9006 (2003), which is hereby incorporated by reference in its entirety). Furthermore, isoform differences in the pro-apoptotic effects of Ras have been observed. For example, whereas K-Ras transformed fibroblasts are sensitized to γ irradiation induced apoptosis, H-Ras transformed cells are protected (Choi et al., "Opposite Effects of Ha-Ras and Ki-Ras on Radiation-Induced Apoptosis Via Differential Activation of PI3K/Akt and Rac/p38 Mitogenactivated Protein Kinase Signaling Pathways," *Oncogene* 23:9-20 (2004), which is hereby incorporated by reference in its entirety). The data demonstrate that activated K-Ras sensitizes cells to the pro-apoptotic effects of PKC agonists in an S181 dependent fashion. Combined with the demonstration that S181 is the principal PKC site on K-Ras, this offers compelling evidence for a pro-apoptotic function of K-Ras phosphorylated at S181. The demonstration that activated K-Ras with a phosphomimetic substitution at position 181 potently induces apoptosis confirms this observation. The finding that K-Ras phosphorylated on S181 is released from the plasma membrane and targets to the endoplasmic reticulum and mitochondria, organelles intimately involved in regulating apoptosis (Kuwana et al., "Bcl-2-Family Proteins and the Role of Mitochondria in Apoptosis," *Curr. Opin. Cell Biol.* 15:699-691 (2003); Scorrano et al., "BAX and BAK regulation of Endoplasmic Reticulum Ca2+: A Control Point for Apoptosis," *Science* 300:135-139 (2003), which are hereby incorporated by reference in their entirety), suggests a cell biological basis for the switch from a pro-survival to a pro-apoptotic molecule. Since K-Ras with a polyglutamine substitution for the polylysine sequence localizes to the ER but does not affect cell viability, the mitoc-hondrial localized phospho-K-Ras must be responsible for pro-apoptotic signaling. The observation that activated K-Ras targeted exclusively to the mitochondrial outer membrane with the Bcl-XL tail is capable of stimulating apoptosis, albeit with a requirement for a negative charge at position 181, demonstrates that such signaling can indeed ensue from the mitochondria. The requirement for a negative charge at position 181 suggests that, in addition to the appropriate membrane platform, a specific protein-protein interaction is required.

K-Ras dissociated from the plasma membrane could trigger apoptosis either by abruptly disengaging from pro-survival signaling down the PI3 kinase pathway or by engaging pro-apoptitic pathways (Cox et al., "The Dark Side of Ras: Regulation of Apoptosis, *Oncogene* 23:8999-9006 (2003); Downward, "Ras Signaling and Apoptosis,"*Curr. Opin. Genet. Dev.* 8:49-54 (1998), which are hereby incorporated by reference in their entirety). The potent pro-apoptotic effect of K-Ras12V181E that was observed in cells with intact endogenous Ras signaling strongly suggests the latter. The best studied pro-apoptotic Ras effectors are the RASSF family of tumor suppressors (Eckfeld et al., "RASSF4/Ado37 Is a Potential Ras Effector/Tumor Suppressor of the RASSF Family," *Cancer Res.* 64:8688-8693 (2004), which is hereby incorporated by reference in its entirety). A dominant negative form of Norel is the best characterized membrane of this family (Khokhlatchev et al., "Identification of a Novel Ras-Regulated Proapoptotic Pathway," *Curr. Biol.* 12:253-265 (2002), which is hereby incorporated by reference in its entirety), was ineffective at blocking K-Ras12V181E stimulated apoptosis. Because Ras proteins have been reported to interact with Bcl-2 family proteins (Rebollo et al., "Bcl-2 Differentially Targets K-, N-, and H-Ras to Mitochondria in IL-2 Supplemented or Deprived Cells: Implications in Prevention of Apoptosis," *Oncogene* 18:4930-4939 (1999), which is hereby incorporated by reference in its entirety) the possibility that this type of interaction might mediate apoptosis was explored. Programmed cell death can be enhanced by positively regulating a pro-apoptotic Bcl-2 family (e.g., Bak, Bax, or Bid) member or inhibiting the action of an anti-apoptotic family member (e.g., Bcl-2 and Bcl-XL). Among these proteins was discovered an interaction between K-Ras and Bcl-XL that was enhanced by phosphorylation or by the presence of a negative charge at position 181. It has further been shown that this interaction takes place on the outer mitochondrial membrane. Therefore, phosphorylated K-Ras promotes apoptosis by interacting with and interfering with the function of BCl-XL on the mitochondria.

Whatever the molecular mechanism of phospho-K-Ras induced apoptosis, this novel pathway is extremely significant since it could be readily exploited to develop anti-cancer drugs that are specific for oncogenic K-Ras driven tumors. This idea has been tested by assessing the anti-neoplastic effects of bryostatin-1, a PKC agonist already used in clinical trials, in limiting the growth of K-Ras dependent tumors. It was found that, whereas bryostatin-1 was effective against tumors in nude mice derived from cells transformed with conventional oncogenic K-Ras12V, it lost its efficacy in tumors driven by K-Ras12V181A. This demonstrates that the anti-tumor action of bryostatin-1 was dependent on S181, shown to be phosphorylated in response to the drug. This result suggests that agents that promote phosphorylation of K-Ras on S181 have the potential to be K-Ras specific anti-cancer agents.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of identifying compounds as candidate drugs for treatment of cancer, said method comprising:
providing a cell expressing a GTPase protein that associates with a membrane via a prenyl lipid in combination with a polybasic region of the protein such that an electrostatic interaction between the GTPase protein and the membrane exists and a prenyl-electrostatic switch is created;
contacting the cell with compounds to be evaluated; and
selecting compounds able to cause partial neutralization of the electrostatic interaction between the GTPase protein and the membrane and thereby activate the prenyl-electrostatic switch, as candidate drugs for treatment of cancer.

2. The method according to claim 1, wherein the GTPase protein is selected from the group consisting of K-Ras, Rap1a, RhoA, Rnd1, Rnd2, and Rnd3.

3. The method according to claim 1 further comprising:
tagging said GTPase protein prior to said contacting.

4. The method according to claim 1, wherein the cell is selected from the group consisting of COS-1, HeLa, MDCK, and Jurkat cells.

5. The method according to claim 1, wherein the electrostatic interaction is between polybasic regions of the GTPase protein and anionic head groups of inner leaflet phospholipids.

6. The method according to claim 1, wherein the polybasic region comprises a region of about 20 amino acids adjacent to a C-terminal CAAX motif.

7. The method according to claim 2, wherein the GTPase protein is K-Ras.

8. The method according to claim 7, wherein the K-Ras protein is splice variant K-Ras4B protein.

9. The method according to claim 8, wherein the prenyl-electrostatic switch in the K-Ras4B protein is in a polybasic region of a C-terminal portion of the K-Ras4B protein.

10. The method according to claim 9, wherein the prenyl-electrostatic switch in the K-Ras4B protein comprises an amino acid residue in the C-terminal portion of the K-Ras4B protein that undergoes phosphorylation.

11. The method according to claim 10, wherein the amino acid residue is serine.

12. The method according to claim 11, wherein the serine is in position 181 of the K-Ras4B protein.

13. The method according to claim 9, wherein the prenyl-electrostatic switch in the K-Ras4B protein comprises at least two amino acid residues in the C-terminal portion of the K-Ras4B protein which undergo phosphorylation.

14. The method according to claim 13, wherein the at least two amino acid residues are two serine residues.

15. The method according to claim 14, wherein the two seine residues are in positions 171 and 181, respectively, of the K-Ras4B protein.

16. The method according to claim 13, wherein one of the at least two amino acid residues is a threonine residue.

17. The method according to claim 16, wherein the threonine residue is in position 183 of the K-Ras4B protein.

* * * * *